(12) United States Patent
Rempel et al.

(10) Patent No.: US 11,058,388 B2
(45) Date of Patent: Jul. 13, 2021

(54) METHOD AND SYSTEM FOR COMBINING MICROSCOPIC IMAGING WITH X-RAY IMAGING

(71) Applicant: Perimeter Medical Imaging, Inc., Toronto (CA)

(72) Inventors: David Rempel, Toronto (CA); Andrew Berkeley, Woodstock (CA); Elizabeth Alice Munro, Toronto (CA); Yaaseen Atchia, Toronto (CA)

(73) Assignee: PERIMETER MEDICAL IMAGING, INC., Toronto (CA)

( * ) Notice: Subject to any disclaimer, the term of this patent is extended or adjusted under 35 U.S.C. 154(b) by 36 days.

(21) Appl. No.: 16/302,885

(22) PCT Filed: May 19, 2017

(86) PCT No.: PCT/CA2017/050609
§ 371 (c)(1),
(2) Date: Nov. 19, 2018

(87) PCT Pub. No.: WO2017/197527
PCT Pub. Date: Nov. 23, 2017

(65) Prior Publication Data
US 2019/0154595 A1    May 23, 2019

Related U.S. Application Data

(60) Provisional application No. 62/339,620, filed on May 20, 2016.

(51) Int. Cl.
*A61B 5/00* (2006.01)
*A61B 6/00* (2006.01)
(Continued)

(52) U.S. Cl.
CPC .......... *A61B 6/5247* (2013.01); *A61B 5/0066* (2013.01); *A61B 6/04* (2013.01);
(Continued)

(58) Field of Classification Search
CPC ....... A61B 6/04; A61B 6/0407; A61B 6/0414; A61B 6/42; A61B 6/4208; A61B 6/4258;
(Continued)

(56) References Cited

U.S. PATENT DOCUMENTS 6,351,513 B1    2/2002    Bani-Hashemi et al.
6,447,163 B1    9/2002    Bani-Hashemi et al.
(Continued)

FOREIGN PATENT DOCUMENTS

DE    10 2006 003 180 A1    8/2007

OTHER PUBLICATIONS

International Search Report and Written Opinion dated Aug. 25, 2017 in International Patent Application No. PCT/CA2017/050609.
(Continued)

*Primary Examiner* — Allen C. Ho
(74) *Attorney, Agent, or Firm* — Hauptman Ham, LLP

(57) ABSTRACT

Various embodiments are described herein for a system and method of integrated X-ray imaging and microscopic imaging of an imaging area having a sample on a sample stage. An X-ray apparatus may be disposed within the imaging area and be configured to acquire X-ray image data of at least a portion of the sample. A microscopic imaging apparatus may be disposed within the imaging area and be configured to acquire microscopic image data of the at least a portion of the sample. In some embodiments, a processing unit may then control the X-ray apparatus to acquire X-ray image data of the at least the portion of the sample, and generate one or more corresponding X-ray images; determine a region of interest (ROI) of the sample based on the
(Continued)

one or more X-ray images; and control the microscopic imaging apparatus to obtain at least one microscopic image based on the ROI.

21 Claims, 25 Drawing Sheets

(51) Int. Cl.
| | |
|---|---|
| G02B 21/36 | (2006.01) |
| G01B 9/02 | (2006.01) |
| G01B 11/00 | (2006.01) |
| G02B 21/00 | (2006.01) |
| G01B 15/00 | (2006.01) |
| A61B 6/04 | (2006.01) |
| G01N 23/18 | (2018.01) |
| G01N 23/06 | (2018.01) |
| G01N 23/083 | (2018.01) |
| G01N 23/087 | (2018.01) |
| G01N 23/04 | (2018.01) |
| A61B 6/12 | (2006.01) |

(52) U.S. Cl.
CPC .......... *A61B 6/0407* (2013.01); *A61B 6/0414* (2013.01); *A61B 6/42* (2013.01); *A61B 6/4208* (2013.01); *A61B 6/4258* (2013.01); *A61B 6/44* (2013.01); *A61B 6/4405* (2013.01); *A61B 6/4411* (2013.01); *A61B 6/4417* (2013.01); *A61B 6/4429* (2013.01); *A61B 6/4435* (2013.01); *A61B 6/4452* (2013.01); *A61B 6/46* (2013.01); *A61B 6/467* (2013.01); *A61B 6/469* (2013.01); *A61B 6/52* (2013.01); *A61B 6/5205* (2013.01); *A61B 6/5211* (2013.01); *A61B 6/5229* (2013.01); *A61B 6/5235* (2013.01); *A61B 6/56* (2013.01); *A61B 6/563* (2013.01); *G01B 9/0203* (2013.01); *G01B 9/02031* (2013.01); *G01B 9/02091* (2013.01); *G01B 11/002* (2013.01); *G01B 15/00* (2013.01); *G01N 23/04* (2013.01); *G01N 23/06* (2013.01); *G01N 23/083* (2013.01); *G01N 23/087* (2013.01); *G01N 23/18* (2013.01); *G02B 21/002* (2013.01); *G02B 21/36* (2013.01); *A61B 5/0035* (2013.01); *A61B 5/0071* (2013.01); *A61B 6/12* (2013.01); *A61B 6/566* (2013.01); *G01N 2223/423* (2013.01); *G01N 2223/427* (2013.01); *G01N 2223/6126* (2013.01)

(58) Field of Classification Search
CPC ....... A61B 6/44; A61B 6/4405; A61B 6/4411; A61B 6/4417; A61B 6/4429; A61B 6/4435; A61B 6/4452; A61B 6/46; A61B 6/467; A61B 6/469; A61B 6/52; A61B 6/5205; A61B 6/5211; A61B 6/5229; A61B 6/5235; A61B 6/5247; A61B 6/56; A61B 6/563; A61B 6/566; A61B 5/0035; A61B 5/0066; G01B 9/0203; G01B 9/02031; G01B 9/02091; G01N 23/04; G01N 23/06; G01N 23/083; G01N 23/087; G01N 23/18
USPC ................................ 378/58, 62, 63; 356/479
See application file for complete search history.

(56) References Cited

U.S. PATENT DOCUMENTS

| | | | |
|---|---|---|---|
| 7,198,404 B2 | 4/2007 | Navab et al. | |
| 7,348,563 B2 * | 3/2008 | Fujita | A61B 5/0066 250/363.04 |
| 7,372,575 B2 * | 5/2008 | Fujita | A61B 5/0062 356/479 |
| 7,428,052 B2 * | 9/2008 | Fujita | A61B 5/0062 356/479 |
| 7,593,559 B2 * | 9/2009 | Toth | A61B 3/0025 128/922 |
| 7,729,746 B2 * | 6/2010 | Redel | A61B 6/466 600/427 |
| 7,785,261 B2 * | 8/2010 | Maschke | A61B 34/20 600/407 |
| 7,872,759 B2 | 1/2011 | Tearney et al. | |
| 8,041,409 B2 | 10/2011 | Leevy et al. | |
| 8,335,557 B2 * | 12/2012 | Maschke | A61B 6/12 378/117 |
| 8,386,015 B2 * | 2/2013 | Kamen | A61B 6/037 382/128 |
| 8,548,567 B2 * | 10/2013 | Maschke | A61B 5/0215 600/427 |
| 8,629,888 B1 * | 1/2014 | Chen | G16H 40/63 345/632 |
| 8,681,116 B2 * | 3/2014 | Merritt | A61B 5/7445 345/173 |
| 9,115,974 B2 * | 8/2015 | Kang | A61B 5/6886 |
| 9,121,926 B2 * | 9/2015 | Nair | A61B 8/06 |
| 9,207,062 B2 * | 12/2015 | Kang | G01B 9/02045 |
| 9,250,060 B2 * | 2/2016 | Kang | G01B 9/02044 |
| 9,347,894 B2 * | 5/2016 | Sims | A61B 6/508 |
| 9,351,698 B2 * | 5/2016 | Dascal | G06T 7/11 |
| 9,582,055 B2 * | 2/2017 | De Jong | G08C 19/00 |
| 9,597,046 B2 * | 3/2017 | Goossen | A61B 5/0073 |
| 9,770,172 B2 * | 9/2017 | Sturm | A61B 5/0037 |
| 9,779,483 B2 * | 10/2017 | Cohen | G06T 5/00 |
| 9,808,148 B2 * | 11/2017 | Miller | A61B 1/0684 |
| 9,907,696 B2 * | 3/2018 | Kang | A61F 9/00736 |
| 9,955,878 B2 * | 5/2018 | Burkett | A61B 5/0215 |
| 10,049,418 B2 * | 8/2018 | Mansker | G06F 19/00 |
| 10,064,584 B2 * | 9/2018 | Yared | A61B 6/508 |
| 10,064,595 B2 * | 9/2018 | Baumgart | A61B 6/5247 |
| 10,172,582 B2 * | 1/2019 | Dascal | G06T 7/0012 |
| 10,175,735 B2 * | 1/2019 | Nool | G06F 13/4081 |
| 10,188,808 B2 * | 1/2019 | Kang | A61M 5/46 |
| 10,213,182 B2 * | 2/2019 | Millett | A61B 5/026 |
| 10,222,204 B2 * | 3/2019 | Yahng | G01B 11/24 |
| 10,231,701 B2 * | 3/2019 | Ryan | A61B 8/445 |
| 10,335,034 B2 * | 7/2019 | Mansker | A61B 6/481 |
| 10,368,836 B2 * | 8/2019 | Merritt | A61B 5/7475 |
| 10,409,951 B2 * | 9/2019 | Mansker | G16H 30/20 |
| 10,441,754 B2 * | 10/2019 | Richardson | A61B 5/0215 |
| 10,453,561 B2 * | 10/2019 | Balignasay | G16H 10/60 |
| 10,489,551 B2 * | 11/2019 | Mansker | G16H 30/00 |
| 10,499,813 B2 * | 12/2019 | Adler | A61B 6/504 |
| 10,666,928 B2 * | 5/2020 | Liu | A61B 90/37 |
| 10,799,209 B2 * | 10/2020 | Lahti | G16H 30/20 |
| 10,869,603 B2 * | 12/2020 | Millett | A61B 8/4416 |
| 10,991,069 B2 * | 4/2021 | Ryu | A61B 6/547 |
| 2003/0082104 A1 | 5/2003 | Mertelmeier | |
| 2007/0115481 A1 | 5/2007 | Toth et al. | |
| 2007/0123771 A1 | 5/2007 | Redel et al. | |
| 2007/0173717 A1 | 7/2007 | Camus et al. | |
| 2007/0238957 A1 | 10/2007 | Yared | |
| 2007/0265521 A1 | 11/2007 | Redel et al. | |
| 2008/0008366 A1 | 1/2008 | Desh et al. | |
| 2008/0062429 A1 | 3/2008 | Liang et al. | |
| 2010/0030069 A1 | 2/2010 | Peter | |
| 2011/0040169 A1 | 2/2011 | Kamen et al. | |
| 2012/0051514 A1 | 3/2012 | Sims et al. | |
| 2012/0095322 A1 | 4/2012 | Tsekos et al. | |
| 2013/0281832 A1 | 10/2013 | Baumgart et al. | |
| 2014/0254900 A1 | 9/2014 | Sturm | |
| 2014/0288420 A1 | 9/2014 | Goossen et al. | |

OTHER PUBLICATIONS

Tu et al., "Fusion of 3D QCA and IVUS/OCT", Int J Cardiovasc Imaging (2011), 27(2): 197-207.
Hebsgaard et al., "Co-registration of optical coherence tomography and X-ray angiography in percutaneous coronary intervention. The

(56) References Cited

OTHER PUBLICATIONS

Does Optical Coherence Tomography Optimize Revascularization (DOCTOR) fusion study", Int J Cardiol. (2015), 182: 272-278.
Hetterich et al., "New X-ray imaging modalities and their integration with intravascular imaging and interventions", Int J Cardiovasc Imaging (2010; Epub 2009), 26(7): 797-808.
"QANGIO OCT Research Edition v1.0", Medis Specials, 2012 (2 pages).
Sun et al., "Segmentation and Correlations of Optical Coherence Tomography and X-ray Imagines for Breast Cancer Diagnostics", J Innov Opt Health Sci. (2013), 6(2): 1350015 (11 pages).
Meerkin et al., "Three-Dimensional Vessel Analyses Provide More Accurate Length Estimations than the Gold Standard QCA", J Interv Cardiol. (2010), 23(2): 152-159.
International Preliminary Report on Patentability dated Nov. 29, 2018 in International Patent Application No. PCT/CA2017/050609.

* cited by examiner

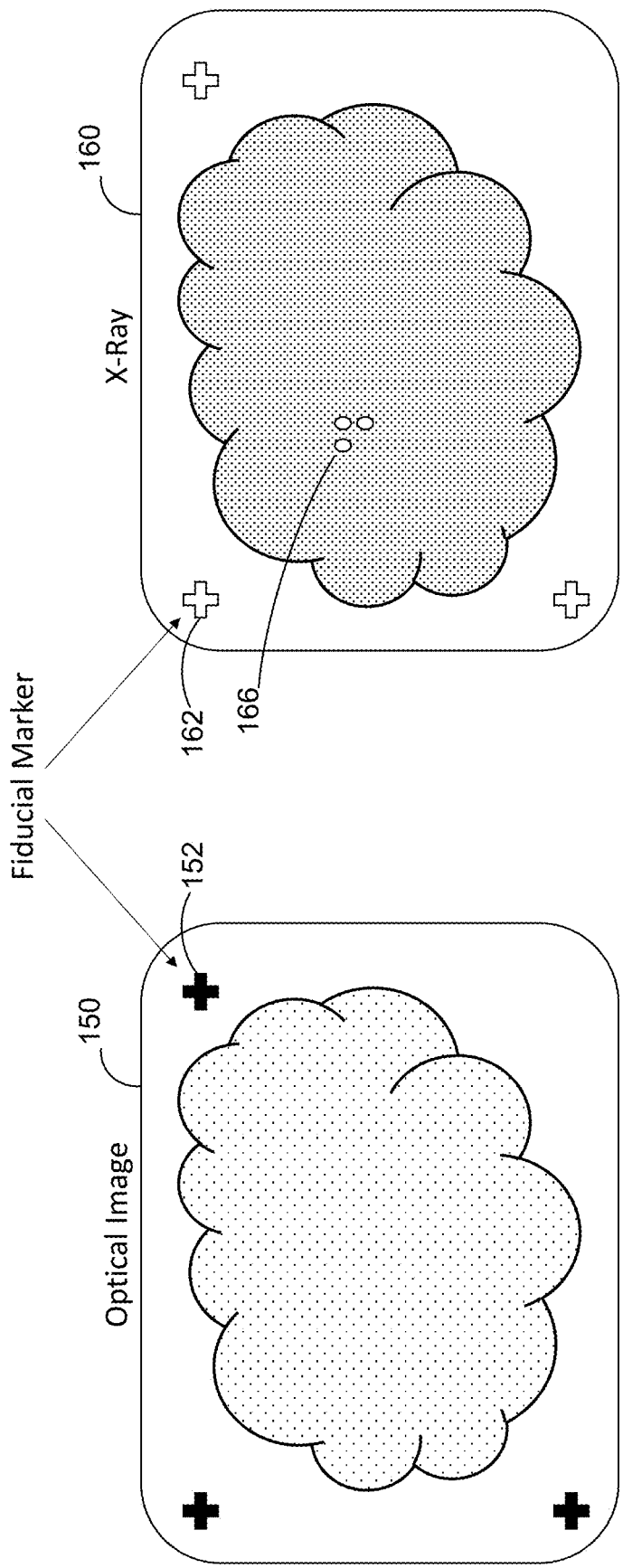

METHOD AND SYSTEM FOR COMBINING MICROSCOPIC IMAGING WITH X-RAY IMAGING

CROSS-REFERENCE TO RELATED APPLICATION

This application is a 35 USC § 371 national stage entry of International Patent Application No. PCT/CA2017/050609, filed May 19, 2017, which claims the benefit of United States Provisional Patent Application No. 62/339,62, filed May 20, 2016, entitled "METHOD AND SYSTEM FOR COMBINING MICROSCOPIC IMAGING WITH X-RAY"; the entire contents of each of which are hereby incorporated herein in their entirety by reference.

FIELD

Various embodiments are described herein for systems and methods for providing multimodal imaging including X-Ray imaging.

BACKGROUND

Various imaging modalities may be used to show different information for an object that is imaged. Typically, separate imaging systems having their own hardware and software are used to obtain images using different imaging modalities.

Optical Coherence Tomography (OCT) imaging is one example of an imaging modality that may be used to obtain an image of an object. OCT imaging uses electro-magnetic radiation to produce high-resolution images of an object such as, but not limited to, tissue, for example. When OCT imaging is performed on an object, optical interferometry is used for depth ranging to obtain topographical and subsurface information for the object. OCT imaging is rapid, non-invasive, and capable of generating 2D or 3D images at high resolution (~10 μm).

X-ray imaging is another example of an imaging modality that may be used to obtain an image of an object. X-ray imaging is a radiation-based imaging technique. X-rays also use light to perform imaging but at a different wavelength compared to other types of imaging. For example, OCT imaging typically operates in the visible to IR regions of the EM spectrum, while X-ray imaging typically operates higher than the visible region of the EM spectrum. X-ray imaging can also be used on tissue. In general, X-ray imaging involves producing an X-ray beam using an X-ray generator and directing the X-ray beam to the object to be imaged. As the X-ray beam passes through the object, parts of the object may absorb the X-ray beam to various extents, thereby resulting in attenuation of different portions of the X-ray beam. An X-ray detector, located on the opposite side of the object (relative to the X-ray generator), captures the attenuated x-ray beam energy, which is then used to produce an X-ray image.

X-ray images can provide different information about an object compared to OCT imaging. For example, X-ray imaging can provide a 2D macroscopic view of the object, showing information (e.g., regions of dense tissue or calcifications within a sample) that is beyond the imaging depth of OCT. On the other hand, OCT imaging provides 3D information with better soft tissue contrast and resolution than X-ray imaging, but only for the exterior 2 mm or so of a target.

SUMMARY OF VARIOUS EMBODIMENTS

In a broad aspect, at least one embodiment described herein provides an integrated system for generating at least one X-ray image and at least one microscopic image of at least a portion of a sample, wherein the system comprises an imaging area having a sample stage for receiving a sample; an X-ray apparatus disposed within the imaging area, the X-ray apparatus being configured to acquire X-ray image data of the at least a portion of the sample; a microscopic imaging apparatus disposed within the imaging area, the microscopic imaging apparatus being configured to acquire microscopic image data of at least a portion of the sample; a processing unit in electrical communication with the X-ray apparatus and the microscopic imaging apparatus, the processing unit being operable to: control the X-ray apparatus to acquire the X-ray image data of at least the portion of the sample, and generate one or more corresponding X-ray images; determine a region of interest (ROI) of the at least a portion of the sample based on the one or more X-ray images; and control the microscopic imaging apparatus to obtain at least one microscopic image based on the ROI.

In at least some embodiments, the X-ray apparatus may comprise a first frame structure, an X-ray generator and an X-ray detector, wherein the X-ray generator and the X-ray detector are mounted to the first frame structure on opposite sides of the sample stage.

In at least some embodiments, the microscopic imaging apparatus may comprise one of an Optical Coherence Tomography (OCT) imaging, Optical Coherence Microscopy imaging, Confocal Microscopy imaging, Spectrally Encoded Confocal Microscopy (SECM) imaging, or fluorescence SECM imaging.

In at least some embodiments, the microscopic imaging apparatus may be an OCT imaging apparatus that comprises a second frame structure and an OCT probe coupled to the second frame structure and oriented towards the sample stage for scanning the at least a portion of the sample during use.

In at least some embodiments, the OCT probe may be disposed above the sample stage or below the sample stage.

In at least some embodiments, the OCT probe may be pivotally adjustable with respect to the sample stage.

In at least some embodiments, the OCT probe may be coupled to a translation assembly that is mounted to the second frame structure, wherein the translation assembly comprises a first translation mechanism for shifting the OCT probe in a first linear direction with respect to the sample stage.

In at least some embodiments, the translation assembly may further comprises a second translation mechanism for shifting the OCT probe in a second linear direction with respect to the sample, the second linear direction being substantially perpendicular to and co-planar with the first linear direction.

In at least some embodiments, the sample stage may comprise a trans-rotational mechanism capable of manipulating the position of the sample stage by applying at least one of a rotational movement and a translational movement.

In at least some embodiments, the trans-rotational mechanism can be controlled to deliver the sample to a first area to be scanned by the X-ray apparatus and a second different area to be scanned by the microscopic imaging apparatus.

In at least some embodiments, the system may comprise an enclosure for housing the imaging area, the X-ray apparatus, the microscopic imaging apparatus, and the processing unit.

In at least some embodiments, the system may further comprise a user interface in electrical communication with the processing unit, wherein the user interface is physically isolated from the imaging area to prevent contamination of the sample during use and the user interface is configured to receive input values that correspond to the ROI and optionally the X-ray imaging parameters, and optionally microscopic imaging parameters.

In at least some embodiments, the microscopic image data may be OCT image data and the controller may be configured to divide the ROI into one or more sub-regions of the sample; and for each of the sub-regions, control the OCT imaging apparatus according to OCT imaging parameters to acquire the OCT image data of the sub-region, and generate a corresponding OCT image based on the OCT image data from the sub-regions.

In at least some embodiments, the OCT image may be an OCT mosaic image that is created using the OCT image data collected over all of the ROI sub-regions.

In at least some embodiments, a time limit may be specified for performing OCT scanning and a scanning density is adjusted to obtain the OCT image data within the time limit.

In at least some embodiments, the system may further comprise a compression plate that is moveable towards the sample stage to compress the sample during imaging.

In another broad aspect, at least one embodiment described herein provides a method for generating at least one X-ray image of at least a portion of a sample and at least one microscopic image of the at least a portion of the sample, wherein the method comprises: positioning the sample on a sample stage within an imaging area; acquiring X-ray image data of the at least a portion of the sample and generating an X-ray image from the X-ray image data; acquiring an optical image data of the at least a portion of the sample and generating an optical image from the optical image data; co-registering the X-ray image and the optical image; determining a Region of Interest (ROI) of the at least a portion of the sample based on at least one of the X-ray image and the optical image; and acquiring microscopic image data of the ROI and generating the microscopic OCT image of the ROI from the acquired microscopic image data.

In at least some embodiments, acquiring OCT image data of the ROI may comprise: dividing the ROI into one or more sub-regions; for each of the sub-regions, acquiring OCT image data of the sub-region; and generating the OCT image using the OCT image data of each of the sub-regions.

In at least some embodiments, acquiring the OCT image data for a given sub-region may comprise determining an initial position for the OCT probe; moving at least one of the OCT probe and the sample stage to place the OCT probe at the initial position; determining a target position for the OCT probe; moving the OCT probe to focus on the target position; and acquiring the OCT image data of the sub-region.

In at least some embodiments, the OCT imaging apparatus may further comprise an optical imaging device and one or more lasers, and wherein the target position for the OCT probe is determined by directing a laser from the one or more lasers to the centre of a scanning window of the OCT probe when the OCT probe is at the initial position; moving the OCT probe towards the sample and taking optical images of the sample using the optical imaging device; adjusting the target position for the OCT probe once a laser spot is in view of the optical imaging device; and recording the target position for the OCT probe once the laser spot appears at a target point on the sample.

In at least some embodiments, determining the target position for the OCT probe may comprise acquiring OCT image data while moving the OCT probe from the initial position to approach the sample; operating the OCT imaging apparatus to detect a maximum signal from the OCT image data; and recording the target position for the OCT probe when the detected maximum signal has crossed a predetermined threshold.

In at least some embodiments, the method may further comprise applying a compression plate to compress the sample between the compression plate and the sample stage.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described. The drawings are not intended to limit the scope of the teachings described herein.

FIGS. 4A and 4B show examples of fiducial markers on optical and X-ray images of a sample, respectively.

Figure 1:
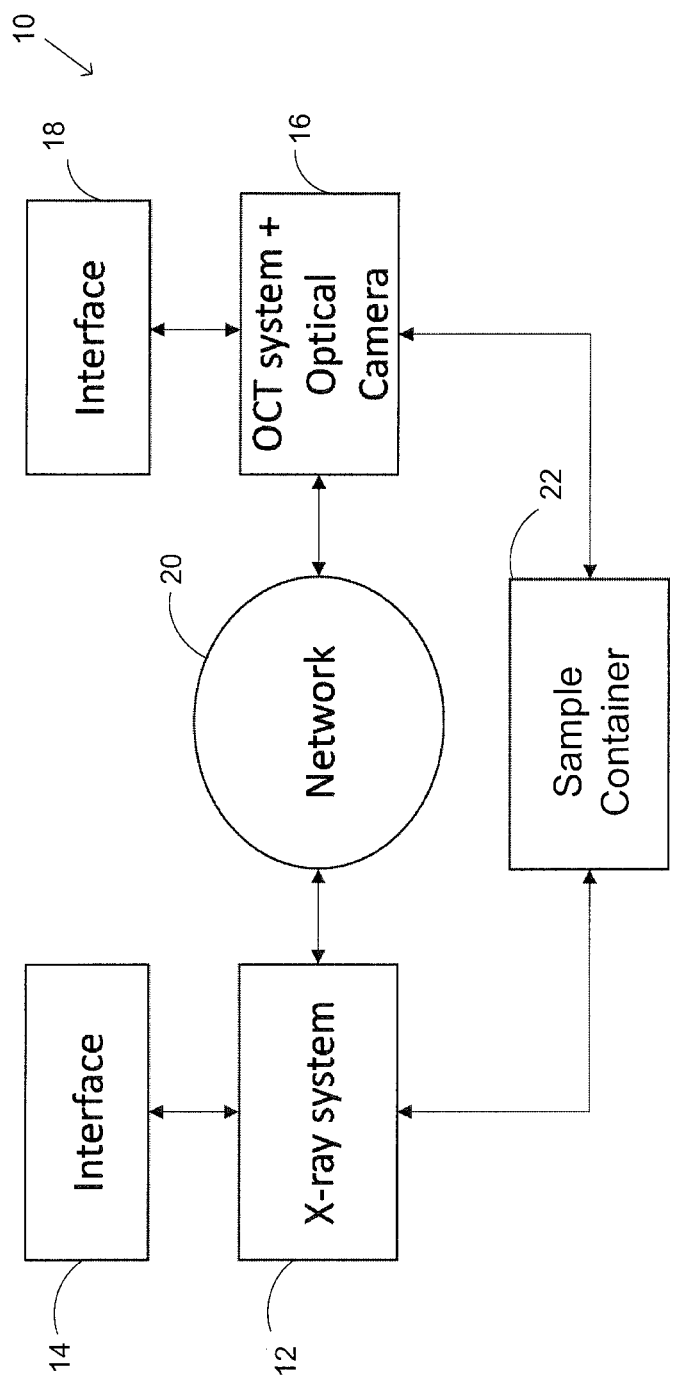
FIG. 1 shows a block diagram for an example embodiment of a non-integrated X-ray and OCT imaging multimodal imaging system, using a sample container having fiducial markers for spatial registration.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to apparatuses or methods having all of the features of any apparatus or method described below or to features common to several or all of the apparatuses and methods described herein. It is possible that there may be an apparatus or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that, as used herein, the wording "and/or" is intended to represent an inclusive-or. That is, "X and/or Y" is intended to mean X or Y or both X and Y, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof that are modified by the term "about" is presumed to mean that a variation is possible of up to a certain amount of the number to which reference is being made if the end result is not significantly changed, such as 10%, for example.

In the following passages, different aspects of the embodiments are defined in more detail. Each aspect so defined may be combined with any other aspect or aspects unless clearly indicated to the contrary. In particular, any feature indicated as being preferred or advantageous may be combined with at least one other feature or features indicated as being preferred or advantageous.

There may be advantages to incorporating X-ray imaging and optical imaging such as OCT imaging, for example, to reduce the footprint when using both devices in an operating room, and to provide fast macroscopic information (via X-ray imaging) to direct the more time consuming microscopic scanning (via optical imaging).

Described herein are various example embodiments of a system and method that can be used to obtain X-ray images and other types of images using a different imaging modality such as at least one of OCT images, Wide Field OCT images and white light images, for example, although other forms of optical imaging may be used in other embodiments as described herein. In at least one of the embodiments described herein, images taken using different imaging modalities may be co-registered.

Image registration in general is a process of aligning multiple images onto a common coordinate system. The images may be obtained by using different sensors, times, depths, or viewpoints, and by using different imaging techniques. Image registration has many potential applications in clinical diagnosis for comparing or integrating medical imaging data obtained using different imaging parameters for a given imaging modality or using different imaging modalities.

Wide field OCT imaging has various applications such as, but not limited to, scanning of a tissue surface that is larger than the viewable area of a typical OCT system. OCT intrinsically has a limited field of view. For example, probe-based OCT systems typically have a field of view of up to 1×1 cm with ~2 mm of depth. However, a typical tissue sample has a surface area of approximately 200 cm². Furthermore, the surface of the tissue may be irregular. At least one of the embodiments of the system and method disclosed herein can be used for wide local excisions.

In at least one embodiment described herein, X-ray imaging may be used to reduce the amount of scanning needed by the OCT probe for OCT imaging. This can be achieved by conducting X-ray imaging on the sample prior to OCT imaging and identifying a region of interest (ROI) on the sample based on one or more features in one or more generated X-ray images. For example, the features can include one or more of regions of high density, regions close to a surgical guide wire or surgical clips, or regions of general abnormalities revealed by the one or more X-ray images. Then, OCT scanning may be performed on the identified ROI rather than the whole surface of the sample thereby reducing data acquisition time.

In at least some embodiments, optical cameras may be included that may be used for using optical imaging on the sample prior to OCT imaging, and an ROI may be identified on one or more obtained optical images based on features visible within those one or more optical images. The term optical image used herein is meant to cover a white light image or a photograph.

In at least some embodiments, at least two of an X-ray image, an optical image and an OCT image for the sample may be co-registered and displayed concurrently to a user, which may provide the user with a more complete picture about the sample than any imaging modality used alone.

It should be noted that although the various example embodiments are described herein with respect to combining OCT imaging with X-ray imaging, in general different microscopic imaging systems, of which OCT is one type, may be combined with X-ray imaging in accordance with the teachings herein. Accordingly, the OCT imaging that is described herein may be replaced by Optical Coherence Microscopy ("OCM") imaging, Confocal Microscopy imaging, Spectrally Encoded Confocal Microscopy ("SECM") imaging, or fluorescence SECM imaging. These microscopic imaging techniques are somewhat similar to one another in that these techniques provide cellular level resolution images of a sample using reflectance from the sample. Each of the microscopic imaging techniques requires a light source (either a broadband light source or a modulated light source) that sends light through a beam splitter, with a portion of the light going to the sample and a portion going to a reference mirror, and then combining reflected light from the sample with the reflected light from the reference mirror to create an interference pattern which is processed to obtain an image. Accordingly, the OCT probe and OCT images that are described in the various embodiments herein may be replaced by a corresponding microscopy probe, such as an OCM probe, for example. However, for ease of illustration, the following examples are described using OCT imaging as the microscopy optical imaging technique.

Referring now to FIG. 1, shown therein is a block diagram for an example embodiment of a non-integrated X-ray and OCT multimodal imaging system 10, which obtains images for at least a portion of a sample in a sample container 22 and uses fiducial markers for spatial registration among the different multimodal images. The non-integrated X-ray and OCT multimodal imaging system 10 comprises a shared sample container 22 containing, for example, excised tissue from a patient, an X-ray system 12 for taking one or more X-ray images of at least a portion of the sample in the sample container 22, and a separate optical system 16 comprising an OCT system for taking one or more OCT images of at least a portion of the sample and optical cameras integrated with the OCT system for taking optical images such as one or more white light images of at least a portion of the sample. In alternative embodiments, the optical cameras may be optional and not be included. The sample may be a tissue specimen. The optical cameras may be standard color cameras. In other embodiments, the samples may be printed electronics circuits that are being non-destructively tested using at least one of the systems and methods described herein.

It should be noted that there may be alternatives of the embodiments described herein in which a sample container may not be used but rather the sample is on a surface, such as a sample stage. When a sample container is used it may be placed on the sample stage.

The non-integrated X-ray and OCT multimodal imaging system 10 further comprises an interface 14 that may be used with the X-ray system 12, and an interface 18 that may be used with the optical system 16. A user may input various system parameter values to the interface 14 or the interface 18 for configuring the X-ray system 12 or the optical system 16, respectively, prior to generating images of the sample using the respective systems. For example, the input parameters may include, but are not limited to, selecting one or more of an ROI, a level of intensity for X-ray generation, and a resolution for OCT imaging, for example.

The X-ray system 12 and the optical system 16 can communicate with each other through a network 20, exchanging data such as fiducial markers and co-registering obtained X-ray image along with optical and/or OCT images of the sample. In addition, some or all of the following data can also be communicated from one system to the other: patient data, a medical record number (MRN), machine ID, time of scan, and fiducial registration information.

Figure 2:
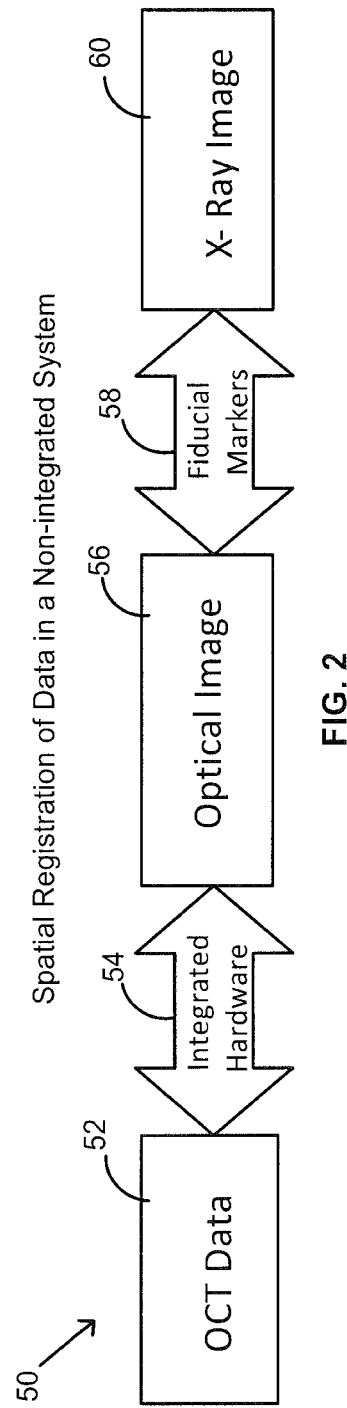
FIG. 2 is a diagram showing how OCT image data or optical image data may be spatially registered to X-ray image data, in a non-integrated multimodal imaging system.

In at least some embodiments, co-registration of the images can be achieved by using fiducial markers in the sample container 22. Referring now to FIG. 2, shown therein is a diagram 50 showing how OCT image data or optical image data may be spatially registered to X-ray image data, in a non-integrated X-ray and OCT multimodal imaging system 10 based on using fiducial markers 58 in the sample container.

The X-ray image 60 of at least a portion of the sample contained in the sample container 22 will show the fiducial markers 58 as will the optical image 56 of the sample. Therefore, the X-ray image 60 and the optical image 56 can be co-registered by aligning the fiducial markers 58 contained in them. On the other hand, the OCT image 52 for at least a portion of the sample will be automatically co-registered with the optical image 56, because the optical cameras are integrated (i.e., by integrated hardware 54) with the OCT system. Therefore, the OCT data 52 can be co-registered with the X-ray image 60 through the optical image 56 when the optical image 56 has already been co-registered with the X-ray image 60.

Referring now to FIGS. 4A and 4B, shown therein are examples of fiducial markers 152 in an optical image 150 and fiducial markers 162 in an X-ray image 160 of a sample, respectively. By aligning the fiducial markers 152 with the fiducial markers 162, the optical image 150 of the sample and the X-ray image 160 of the sample can be spatially co-registered.

Figure 3:
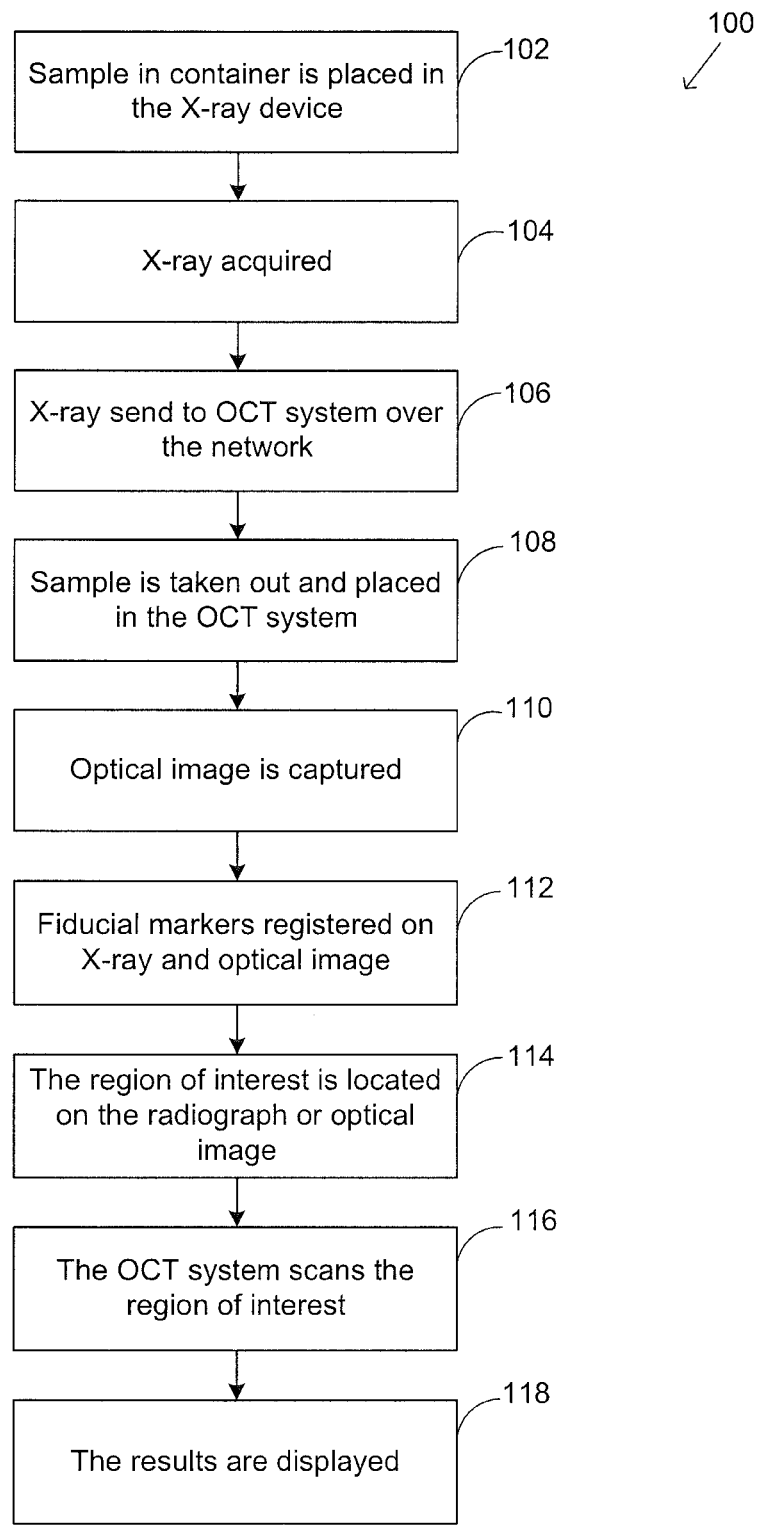
FIG. 3 shows a flowchart of an example embodiment of a method for obtaining OCT and X-ray image data of at least a portion of a sample using a non-integrated imaging system and co-registering the X-ray and OCT image data using the sample container with fiducial markers.

Reference is now made to FIG. 3, which shows a flowchart of an example embodiment of a method 100 for spatial registration of images obtained in a non-integrated X-ray and OCT multimodal imaging system 10, using a sample container 22 with fiducial markers to co-register images obtained using these different imaging modalities. It should be noted that the flowchart illustrates only one example embodiment for the method 100 and there can be other embodiments in which different actions may be included or some actions may be removed depending on the particular application of the non-integrated X-ray and OCT multimodal imaging system 10 (this also applies to the other flowcharts and block diagrams shown and described herein).

Figure 5C:
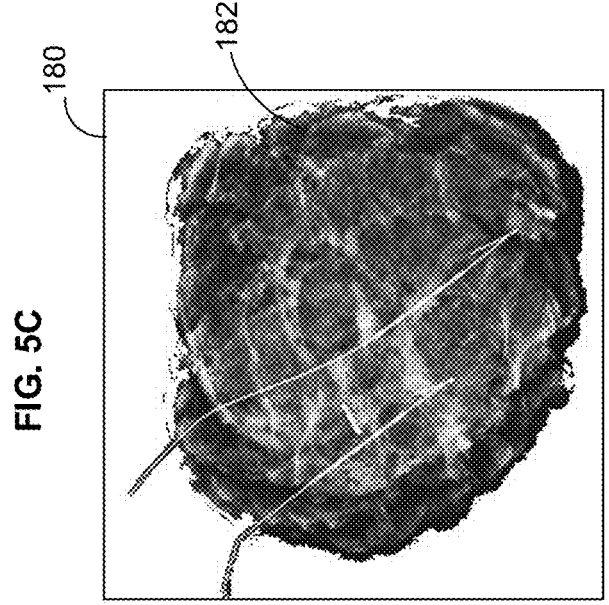
FIG. 5C shows an example schematic of an X-ray image of the sample, showing calcifications.
Figure 5D:
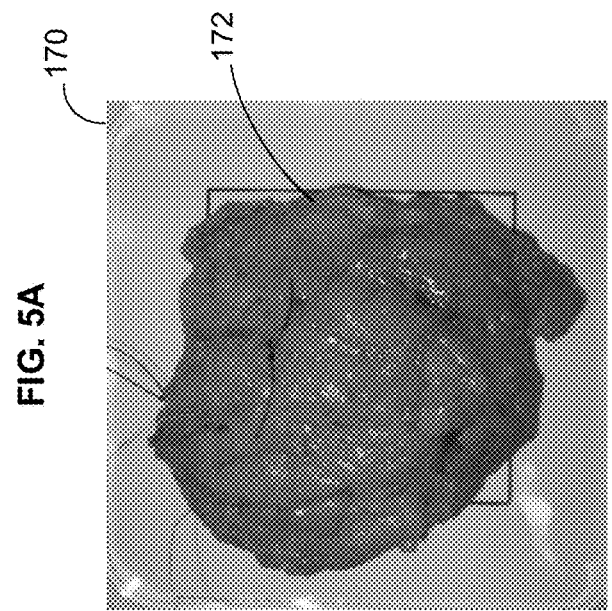
FIG. 5D shows an example of an X-ray image of the sample.

At 102 of method 100, a sample of excised tissue resected from a patient can be placed in the X-ray system 12. At 104, at least one X-ray image can be acquired for a ROI for at least a portion of the sample (see FIG. 5D for an example X-ray image of a sample and FIG. 5C for an example schematic of the actual X-ray image in FIG. 5D).

Figure 5A:
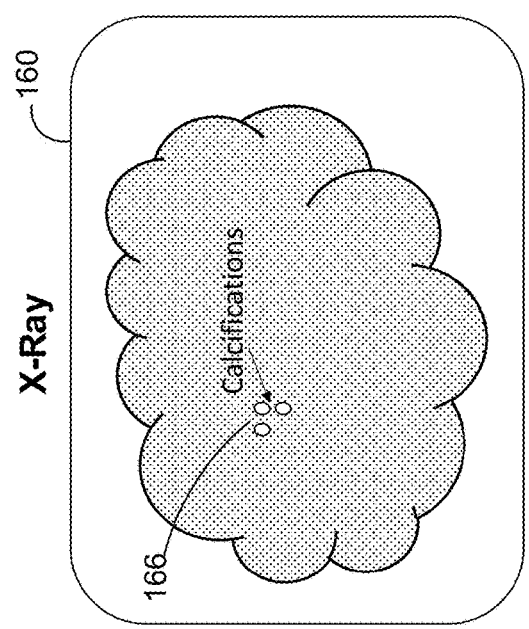
FIG. 5A shows an example schematic view of an optical image of a sample.
Figure 5B:
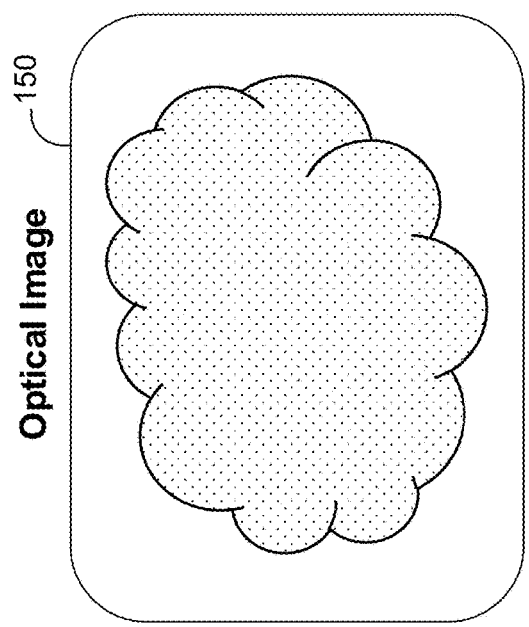
FIG. 5B shows an example of a white light image of the sample.

At 106, the X-ray images that are obtained can be sent over the network 20 to the optical system 16. At 108, the sample container 22 with the sample is taken out from the X-ray system 12 and placed in the optical system 16. The optical system 16 has integrated optical cameras. At 110, at least one optical image of at least a portion of the sample can be taken using the optical cameras (see FIG. 5B for an example actual white light image of a sample and FIG. 5A for an example schematic of the actual white light image of FIG. 5B).

At 112, the optical system 16 can co-register the obtained X-ray images with the corresponding obtained optical images by aligning the fiducial markers on the respective images. In some embodiments, such co-registration, or in other words, fiducial registration, can be achieved by manual calibration. For example, the sample container can be placed in the X-ray system 12 at a fixed location; an X-ray image including the fiducial markers can be obtained and displayed to the user in a software interface (see for example FIG. 6A); the user can identify the fiducial markers using the software interface (e.g., by clicking on the fiducial markers one by one using the software interface); the pixel-to-fiducial locations can be calibrated and saved; and then these pixel-to-fiducial location calibrations can be sent with the obtained X-ray image to the optical system 16. A similar process can be performed in the optical system 16 and the calibrated fiducial registrations can be made with an obtained OCT image and then sent to the X-ray system 12. In both cases, pixel-to-fiducial locations are saved in a calibration file and may be sent with the obtained image to the other imaging system.

In some embodiments, fiducial registration can be achieved by automatic registration. In this case, no calibration is required and the X-ray system 12 and the optical system 16 can automatically detect the fiducial markers using computer vision and automatically register the fiducial markers. In some embodiments, QR codes can be used in each of the corners as described by Luiz F. F. Belussi and Nina S. T. Hirata "Fast QR Code Detection in Arbitrarily Acquired Images" published in 2011 24th SIBGRAPI Conference on Graphics, Patterns and Images, pp. 281-288.

At 114, a user of the non-integrated system 10, such as a clinician, can identify an ROI in one of the obtained X-ray images based on one or more features visible in that X-ray image. These features may include, but are not limited to, calcifications, regions of high density, regions close to a surgical guide wire or surgical clips, and general visible abnormalities, for example. Alternatively, the user may identify the ROI from one of the obtained optical images based on features visible in that optical image. Then, at 116, the optical system 16 can be configured to scan the ROI of the sample. At this point, a time limit for the scan can be set, and the scanning density (i.e., number of cross-sectional images taken in a volume) can be adjusted to obtain the OCT data within the time limit.

At 118, the results can be displayed on a software interface of the system 10 for further examination. The results that are displayed may include the OCT image as well as one or more of the X-ray image and the optical image that were used to define the ROI. In some embodiments, a ruler tool is provided in the software interface so that the user may measure distances in at least one of the windows having the X-ray image, the optical image or the OCT image using the ruler tool. If the user zooms in or zooms out on a displayed image, the ruler tool scales appropriately.

Figure 6A:
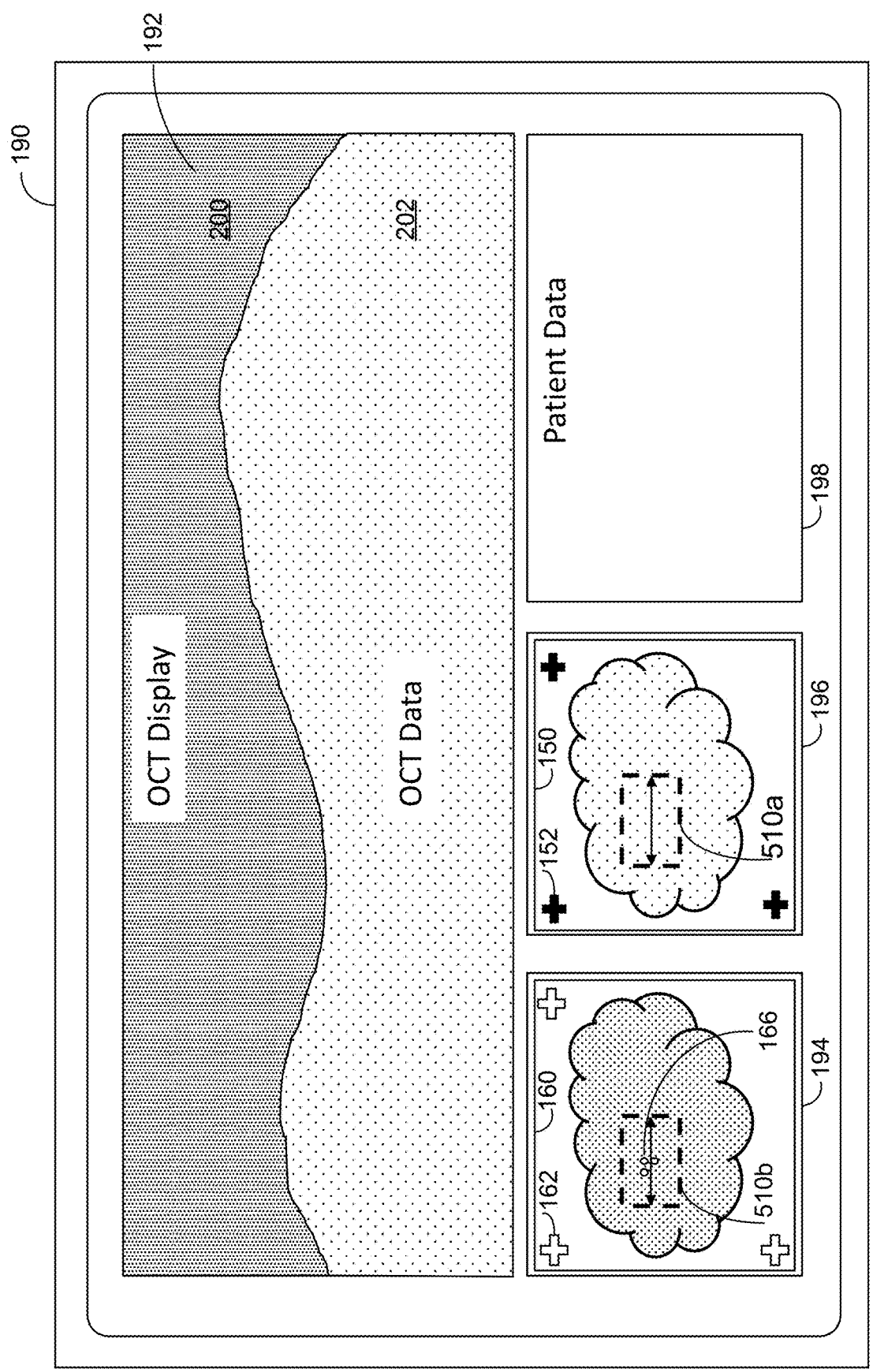
FIG. 6A is an example embodiment of a software interface that may be used with the non-integrated multimodal imaging system showing spatially registered X-ray and optical images based on fiducial markers, and OCT data (the horizontal arrows in the x-ray view and the optical view show where the OCT data is taken).
Figure 6B:
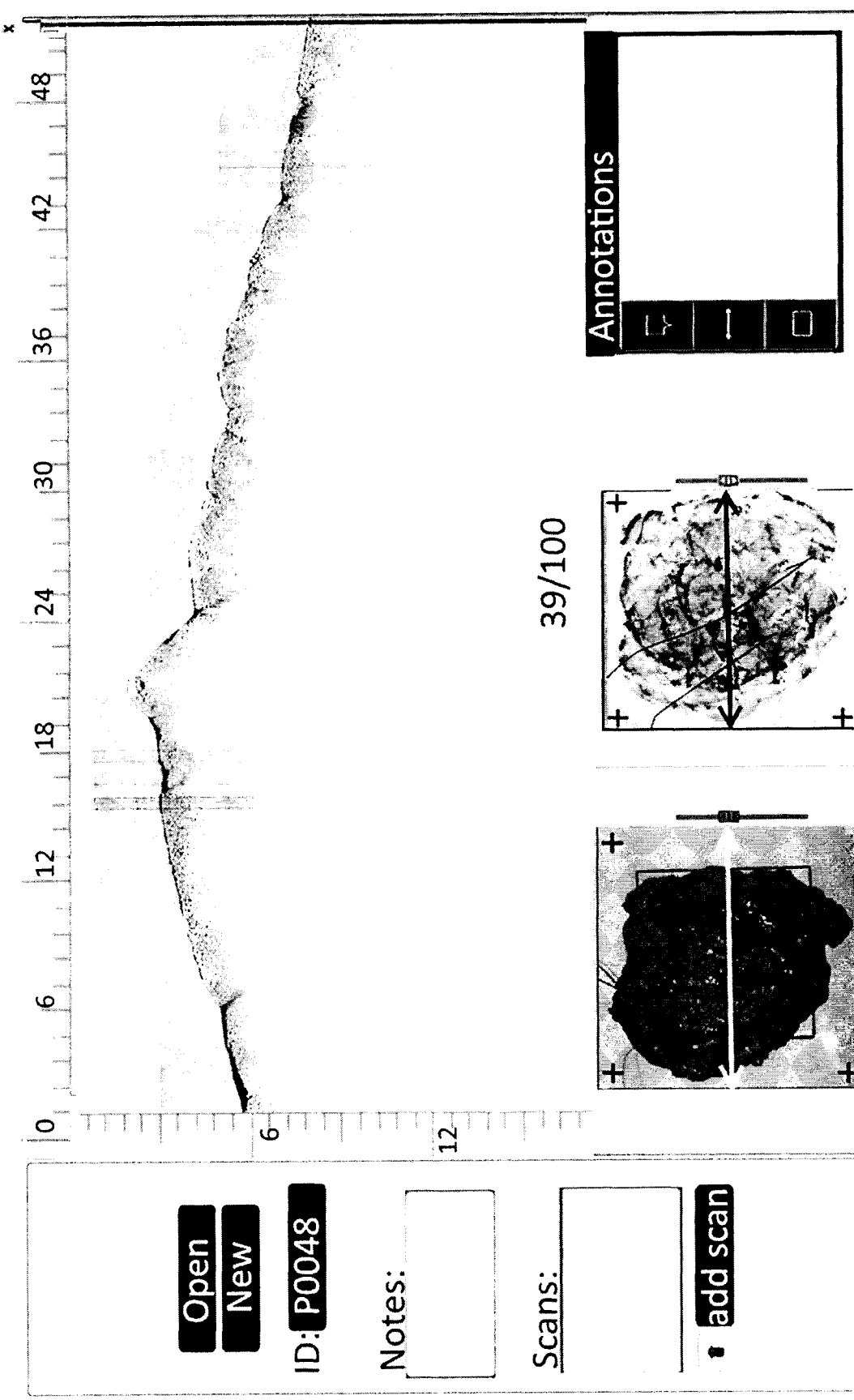
FIG. 6B shows an example embodiment of a software interface for the non-integrated multimodal imaging system.

Referring now to FIG. 6A, shown therein is an example embodiment of a software interface 190 that may be used with the non-integrated multimodal imaging system 10. The software interface 190 has a main window with a first sub-window 194 where an X-ray image 160 of the sample is displayed with fiducial markers 162. The software interface 190 also includes a second sub-window 196 where a co-registered optical image 150 of the sample is displayed with fiducial markers 152. The software interface 190 also includes a third sub-window 198 wherein additional patient information may be displayed; and an OCT sub-window 192 for displaying the obtained OCT data showing the surface of the sample (see the boundary line between 200 and 202). The horizontal arrows in the X-ray image 160 and the optical image 150 show ROIs 510b and 510a, respectively, where the OCT data 192 is taken. In this case, the ROI 510b was defined based on calcifications 166 that are visible in the X-ray image 160. FIG. 6B provides an example implementation of the software interface 190 with X-ray, optical and OCT images that show the same ROI and correspond with one another. In alternative embodiments, any of windows 192, 194, 196, or 198 may be optional or a sub-window for an optical image can be added.

Figure 7:
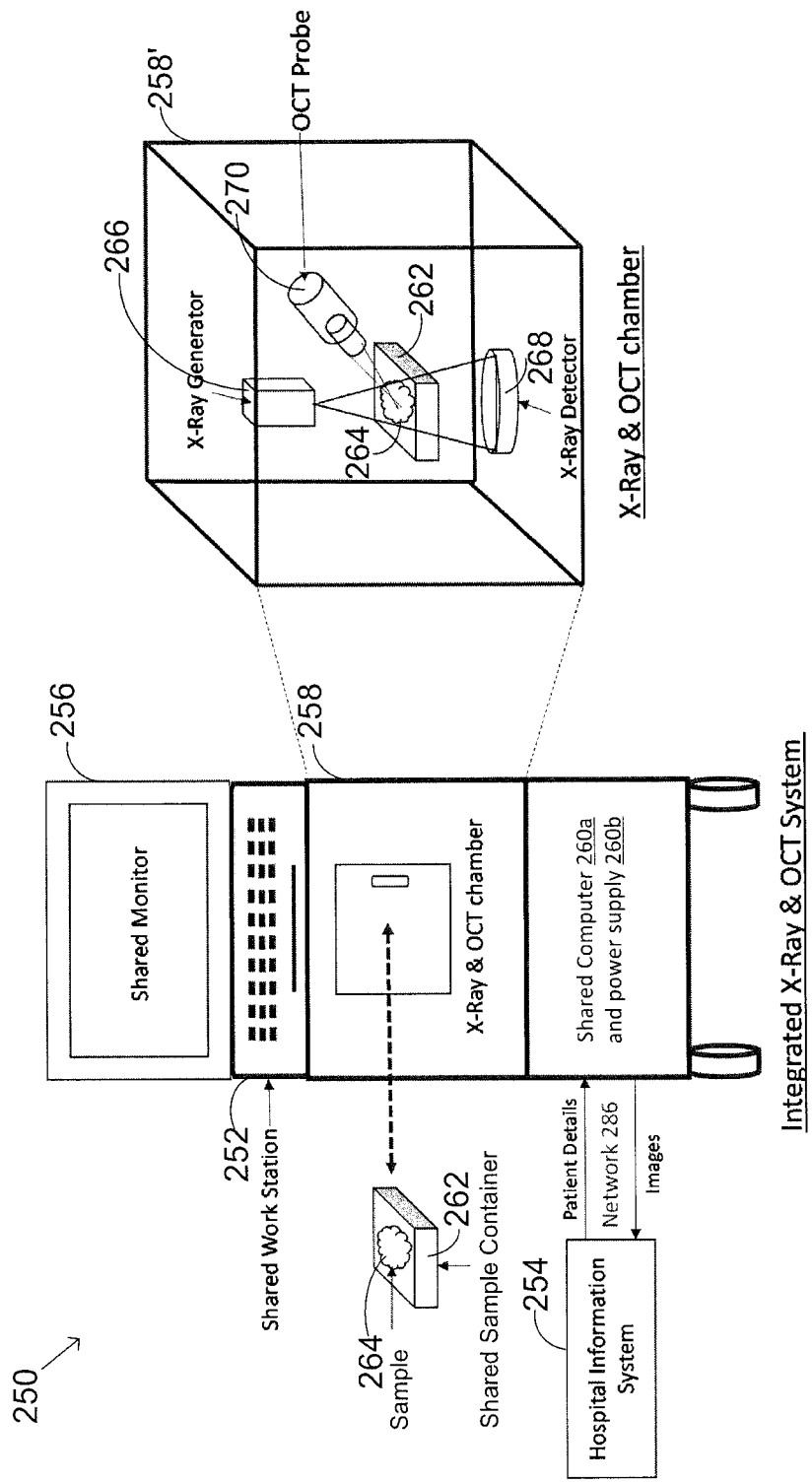
FIG. 7 is a diagram of an example embodiment of an integrated X-ray and OCT multimodal imaging system.
Figure 8:
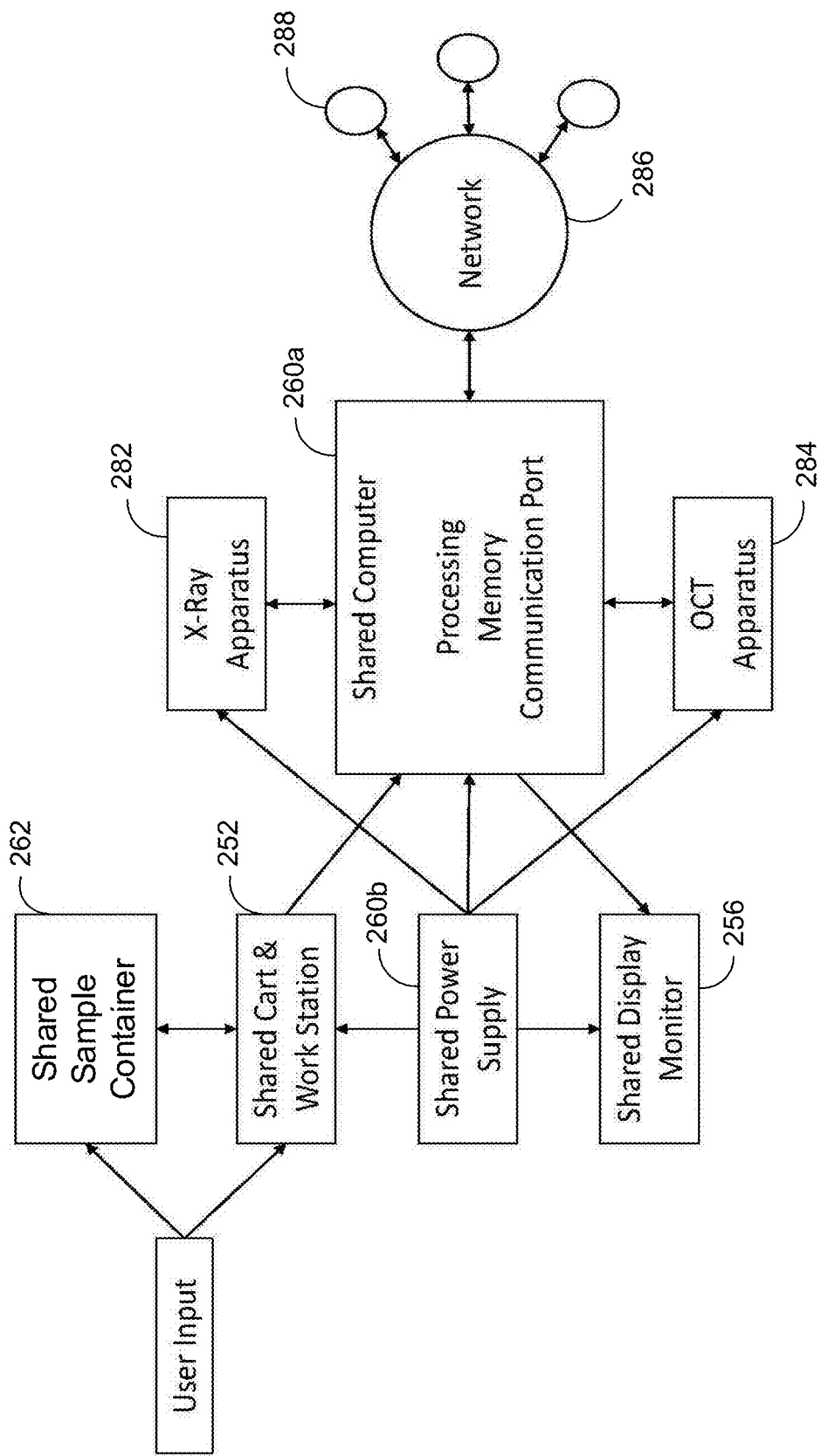
FIG. 8 is a schematic diagram of the integrated multimodal imaging system of FIG. 7.

Referring now to FIGS. 7 and 8, shown therein is a schematic of an example embodiment of an integrated X-ray and OCT multimodal imaging system 250 and a corresponding block diagram, respectively. The integrated X-ray and OCT multimodal imaging system 250 comprises an imaging chamber 258 (i.e. the X-ray and OCT imaging chamber), a shared monitor 256, a shared work station 252, and a shared computer 260a and power supply 260b. The imaging chamber 258 contains an X-ray apparatus 282 and an OCT imaging apparatus 284. The shared power supply 260b can provide power to both the X-ray apparatus 282 and the OCT imaging apparatus 284. The shared computer 260a can comprise a processing unit, a memory, and a communication port (all not shown) through which the shared computer 260a can connect to a network 286 of one or more workstations 288. In some embodiments, the network 286 may be coupled to a Hospital Information System 254 with which the integrated X-ray and OCT multimodal imaging system 250 may exchange images obtained for patients and other information about the patients.

An excised tissue sample 264 may be placed into or onto a shared sample container 262. The shared sample container 262 can be used to maintain the sample 264 in a particular orientation. The shared sample container 262 can be placed in the imaging chamber 258 of the integrated X-ray and OCT multimodal imaging system 250 so that it can be imaged using different imaging modalities. The shared sample container 262 can be used for a variety of purposes, including loading the sample 264 into the integrated X-ray and OCT multimodal imaging system 250, securing the sample 264 during various types of imaging and scanning including X-ray and OCT imaging, transporting the sample 264 from one imaging modality to another within the imaging chamber 258 (for example, from x-ray imaging to OCT imaging), and transporting the sample 264 through the clinical process. The sample 264 may be a tissue specimen or other another object or type of material requiring X-ray and/or OCT imaging.

After the shared sample container 262 is placed inside the imaging chamber 258, the integrated X-ray and OCT multimodal imaging system 250 can then create X-ray images and/or OCT images of at least a portion of the sample 264 using the X-ray apparatus 282 and/or the OCT imaging apparatus 284 contained therein. The X-ray apparatus 282 may generally comprise an X-ray generator 266 that is directed towards the sample 264 in the shared sample container 262 and an X-ray detector 268 disposed on the other side of the shared sample container 262 for capturing the x-ray beams that pass through and are attenuated by the sample 264 in order to obtain the X-ray image data. The OCT imaging apparatus 284 may generally comprise an OCT probe 270 that is directed towards the sample 264 and may be moveable for scanning the sample 264 in order to obtain OCT image data. More details on the X-ray imaging components and the OCT imaging components within the imaging chamber 258 are described with respect to FIGS. 9-11.

The integrated X-ray and OCT multimodal imaging system 250 may operate based on input parameters provided by the user, such as a medical practitioner (e.g., a surgeon, a clinician or a pathologist). Prior to generating images of the sample 264, the integrated X-ray and OCT multimodal imaging system 250 may first receive input parameters from the user to specify various operational parameters for the X-ray and/or OCT image data to be generated. For example, the input parameters may include, but are not limited to, intensity level for the X-ray generator 268 and/or the light source used by the OCT imaging apparatus 282, sampling resolution for digitizing image data that is obtained, the number of images to be obtained, parameters that define the ROI, and the orientation of the sample (i.e., superior, inferior, posterior, anterior, dorsal, proximal, medial or lateral), for example. In some embodiments, the imaging may be totally automated and these parameters may be predefined.

The X-ray apparatus 282 of the integrated X-ray and OCT multimodal imaging system 250 comprises a first frame structure to which the X-ray generator 268 and the X-ray detector 268 are mounted such that the X-ray generator 268 and the X-ray detector 268 are on opposite sides of the shared sample container 262 for obtaining at least one X-ray image of the sample 264 during use. The OCT imaging apparatus 284 of the integrated X-ray and OCT multimodal imaging system 250 comprises a second frame structure to which the OCT imaging probe 270 is coupled and oriented so that the OCT imaging probe 270 is directed towards the shared sample during use.

In some embodiments, the integrated X-ray and OCT imaging system can have stationary components that are mounted to the first and second frame structures and the sample 264 may be moved during at least one of the imaging stages. For example, in FIGS. 9A and 9B, imaging systems 300a and 300b are shown which include imaging components of an X-ray system 304, i.e. an X-ray source 306 and an X-ray detector 308, that are stationary and imaging components of an OCT system 310, i.e. an OCT probe 312, that is stationary. In this embodiment, the multimodal imaging systems 300a and 300b further comprise optical components for performing white light imaging such as an optical camera 314, which is also stationary. The systems 300a and 300b also comprise an integrated system control module 302, a motion controller module 318 and a translation mechanism 320. The integrated system control module 302 is coupled to the motion controller 318 for sending controls signals to the motion controller 318 in order move a sample stage 322 (upon which the sample 264 is placed) using the translation mechanism 320.

In at least one embodiment, the translation mechanism 320 typically includes a motor and a mechanical linkage (both not shown) to linearly translate the sample stage 322. The motion controller 318 may include a motor driver controller (not shown) for providing current and voltage control signals to the motor. The mechanical linkage may comprise an expandable shaft, a rack and pinion arrangement or a cam system to provide the linear translation.

In an example scenario, initially the sample 264 is placed within or on the shared sample container 262 and the shared sample container 262 is placed on the sample stage 322. The sample stage 322 is positioned so that is between the X-ray source 306 and the X-ray detector 308 so that at least one X-ray image can be taken of at least a portion of the sample 264. The integrated system control module 302 can then control the motion controller 318 to actuate the translation mechanism 320 so that it moves the sample stage 322 away from the X-ray apparatus components and to a predetermined target position that is in the range of the OCT probe 312. Once the sample 264 is moved to the target position, OCT image data may then be obtained for the sample 264.

Figure 9A:
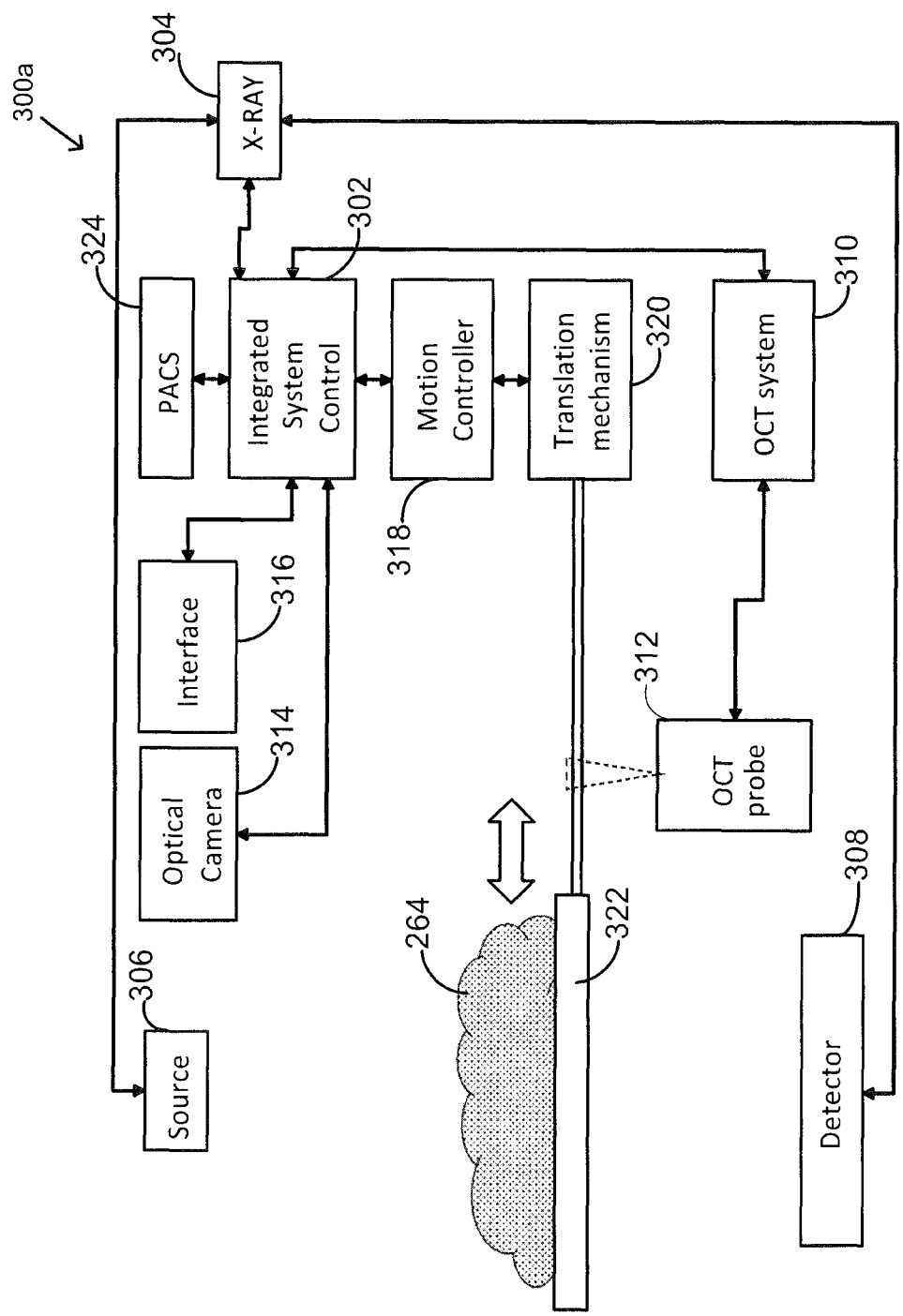
FIG. 9A shows an example embodiment for an arrangement of imaging components for an integrated multimodal imaging system in which the optical components are stationary and the sample stage is moveable.
Figure 9B:
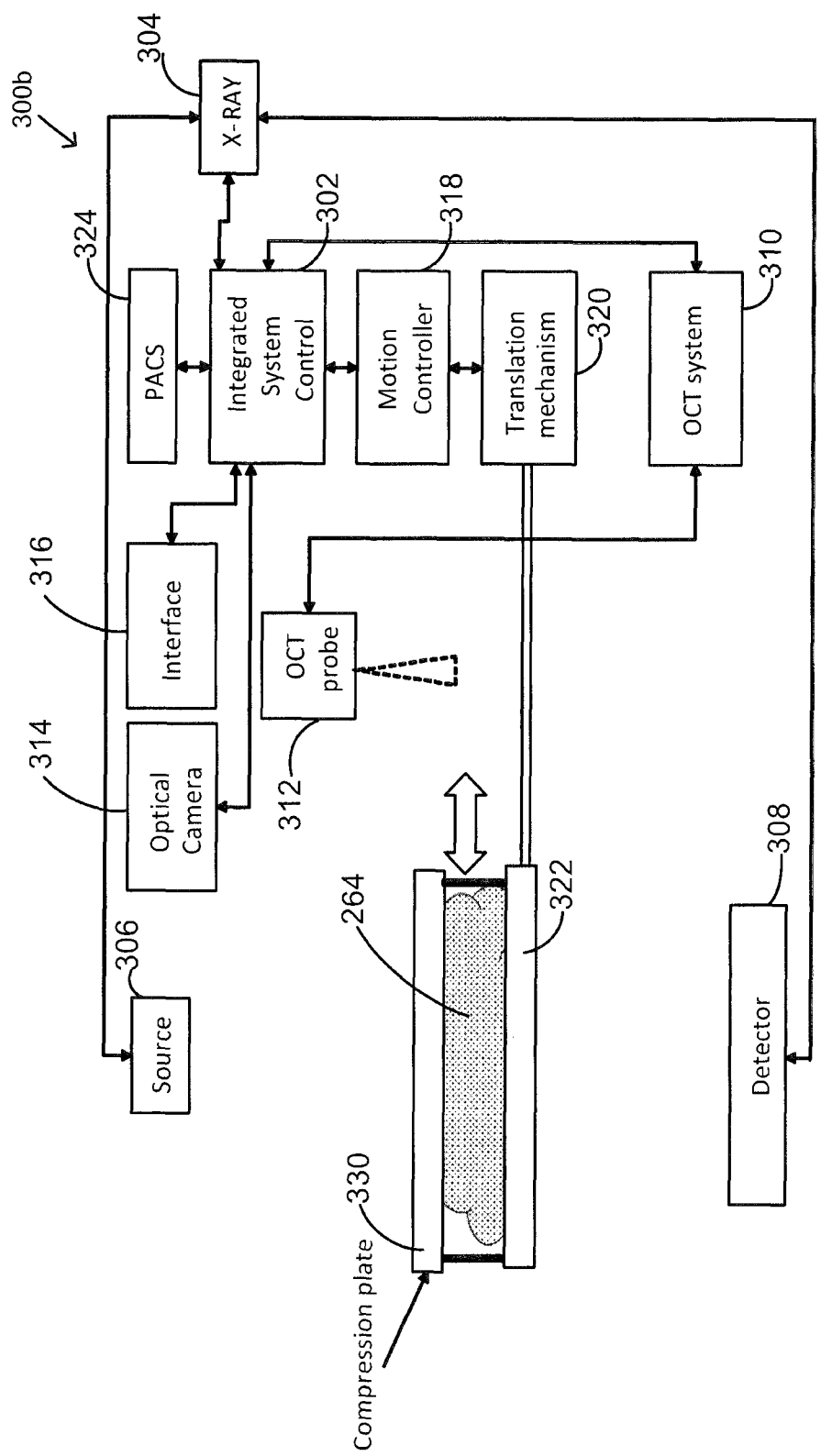
FIG. 9B shows another example embodiment for an arrangement of imaging components for an integrated multimodal imaging system with stationary optical components and a moveable sample stage along with a compression plate.

In some embodiments, as shown in FIG. 9A, the OCT probe 312 can be located below the sample stage 322 and the sample 264 to obtain OCT image data from under the sample 264. In other embodiments, the OCT probe 312 may be placed in a different location to obtain OCT image data from a different direction relative to the sample stage 322 and the sample 264. For example, in FIG. 9B, the OCT probe 312 is placed above the sample stage 322. The imaging system 300b may further comprise a compression plate 330 which can limit the height of the sample 264 and increase the amount of sample 264 that is pressed up against the compression plate which may improve imaging quality and may also help with image registration, and make the scanning pattern more simple because only 2D movements are needed (as one does not have to compensate for height changes during OCT scanning when sufficient compression is applied to the sample 264). For example, the compression plate 330 may be a cover slide. It should be known that in alternative embodiments the systems shown in FIGS. 9A, 10A and 10B can be modified to use a compression plate similar to the compression plate 330 shown in FIG. 9B.

Figure 10A:
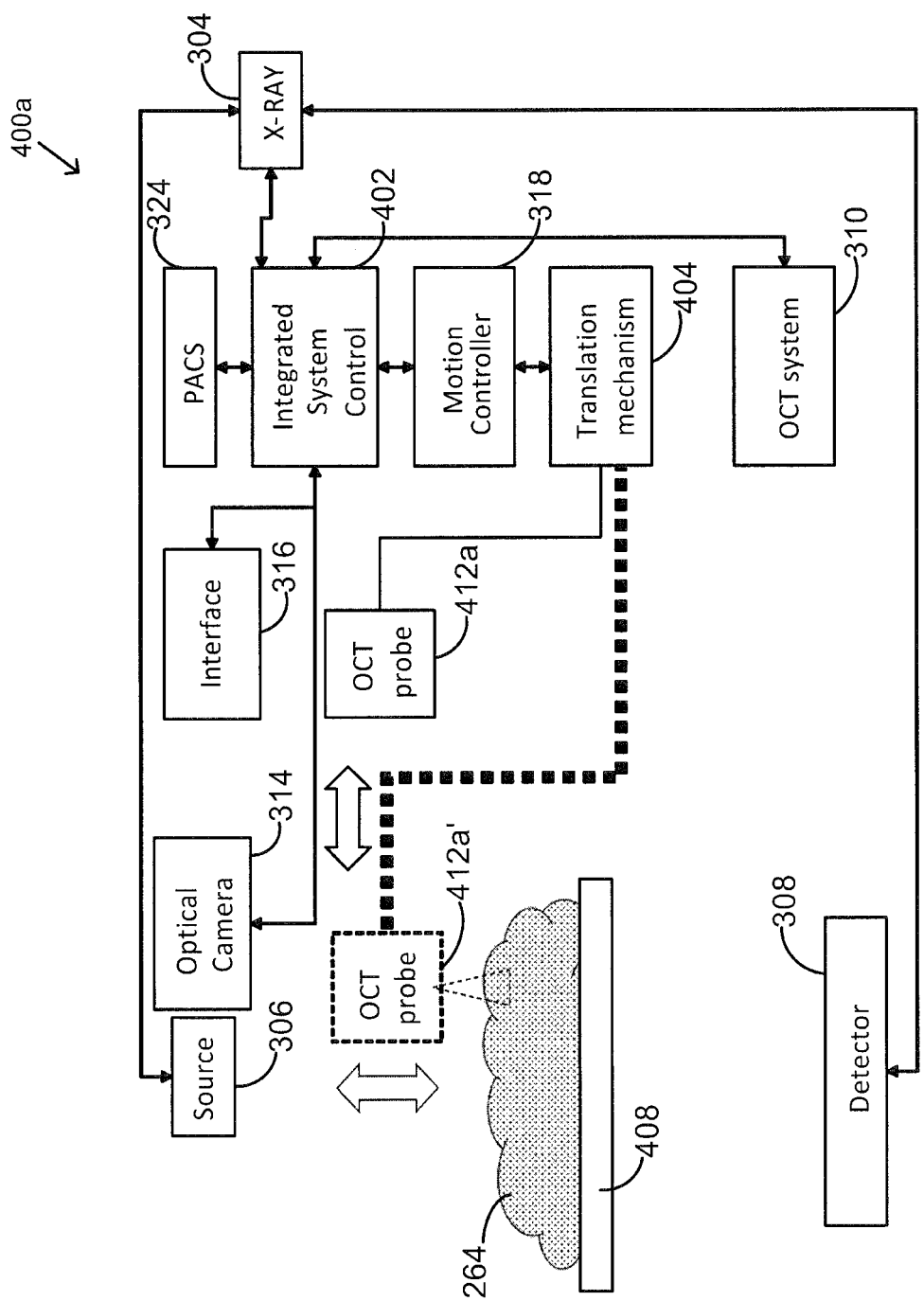
FIG. 10A shows another example embodiment for an arrangement of imaging components for an integrated multimodal imaging system with a moveable OCT probe.
Figure 10B:
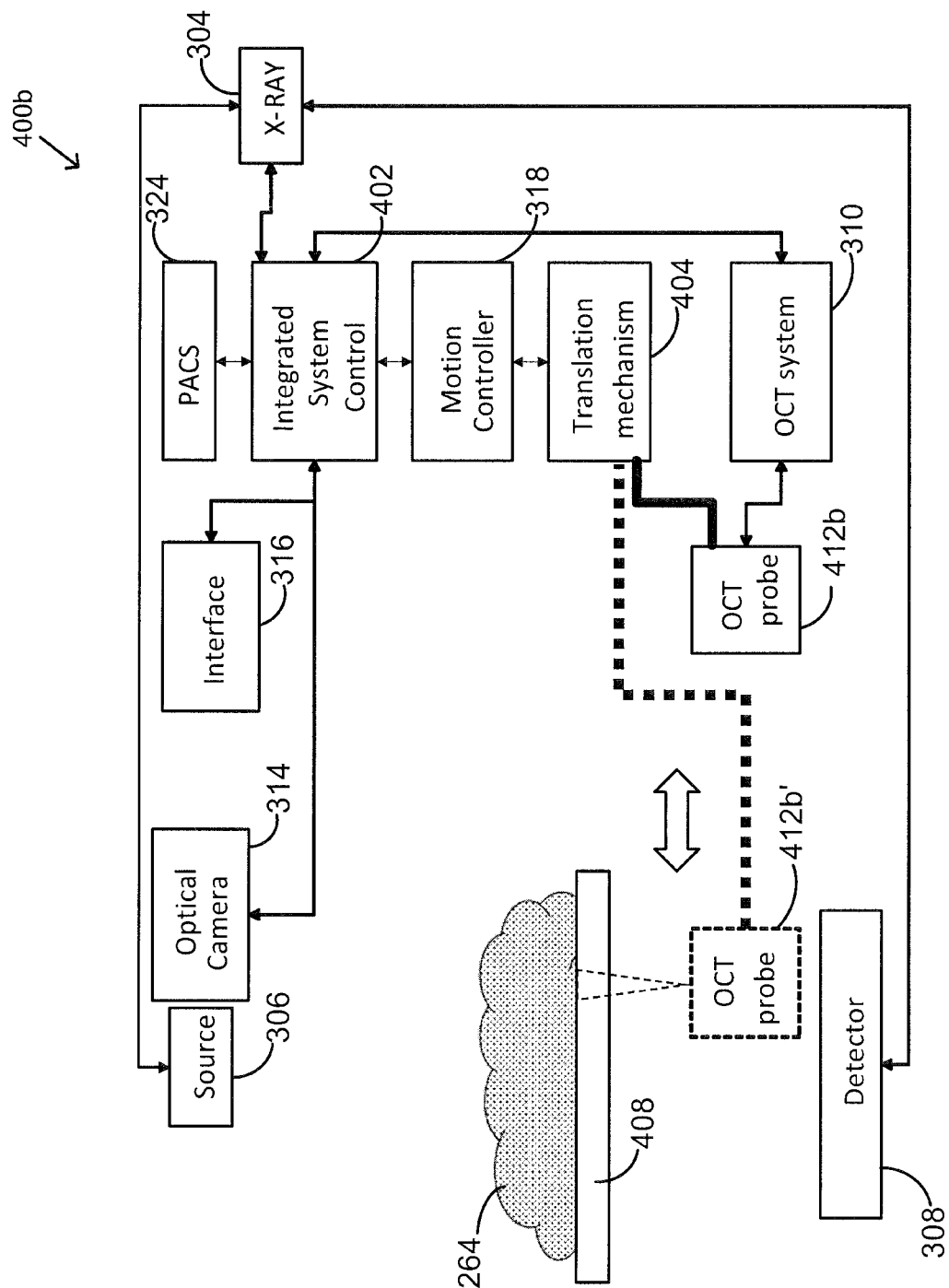
FIG. 10B shows another example embodiment for an arrangement of imaging components for an integrated multimodal imaging system with a moveable OCT probe.

In some other embodiments, the integrated x-ray and OCT imaging system 250 can have a stationary sample stage and moving optical components that are movingly coupled to the second frame structure. Referring now to FIGS. 10A and 10B, shown therein are example embodiments of multimodal imaging systems 400a and 400b with a moveable OCT probe 412a and 412b, respectively, whereas the sample stage 408, the sample 264, the X-ray source 306, the X-ray detector 308, and the optical camera 314 are stationary. The integrated systems control module 402 in systems 400a and 400b is coupled with a motion controller module 318 so that the control module 402 can control the motion controller module 318 to move the OCT probe 412a or 412b using a translation mechanism 404. In some embodiments, the OCT probe 412a or 412b can be moved linearly in 2 dimensions. In some other embodiments, for example, in system 400a shown in FIG. 10A, the OCT probe 412a or 412b can have more degrees of freedom (3D linear and/or rotational movement) to scan the edges of the sample 264. The translated positions of the OCT probe 412a or 412b are represented with references labels 412a' and 412b', respectively.

Furthermore, although not shown in the figures herein, there can be alternative embodiments in which the integrated X-ray and OCT imaging system 250 can also have a moving X-ray source and a moving X-ray detector, in which the movement can be at least one of 1 D linear movement, 2D linear movement, 3D linear movement and rotational movement. In these embodiments, the X-ray source and the X-ray detector are movingly coupled to the first frame structure. In an alternative embodiment, both the X-ray components and the optical components may be movingly coupled to the first and second frame structures, respectively, so that the X-ray components and the optical components can move with respect to the sample stage 322.

In an example scenario, initially the OCT probe 412a is placed outside the field of view of the X-ray apparatus, and the sample 264 can be placed between the X-ray source 306 and the X-ray detector 308 to allow one or more X-ray images to be taken of at least a portion of the sample 264. The control module 402 can then control the motion controller 318 to actuate the translation mechanism 404 to move the OCT probe 412a to a predetermined target position (see OCT probe position 412a') so that the sample 264 is in the range of the OCT probe for imaging. OCT image data may then be obtained for at least a portion of the sample 264. When the OCT probe 412a is no longer in use, it can be moved to its initial position or to a different position outside of the field of view of the X-ray apparatus.

In some embodiments, as shown in FIG. 10A, the OCT probe 412a is located above the sample stage 408 and the sample 264 to obtain OCT image data. In some other embodiments, the OCT probe may be placed in a different location to obtain OCT image data from a different direction relative to the sample stage 408 and the sample 264. For example, in FIG. 10B the OCT probe 412b is placed below the sample stage 408.

In FIGS. 9A, 9B, 10A and 10B, the imaging systems 300a, 300b, 400a and 400b further comprise a user interface module 316 and a picture archiving and communication system (PACS) module 324. In some embodiments, the PACS module 324 is optional. The user interface module 316 allows a user to interact with the systems 300a, 300b, 400a, 400b and control the type of imaging that is performed, the imaging parameters that are used to obtain the image data, and display parameters that are used to process the image data for display on an output screen or on a hardcopy. The PACS module 324 may be used to store images that are obtained using the different imaging modalities as well as access images that have been previously obtained using the multiple imaging modalities.

Figure 11:
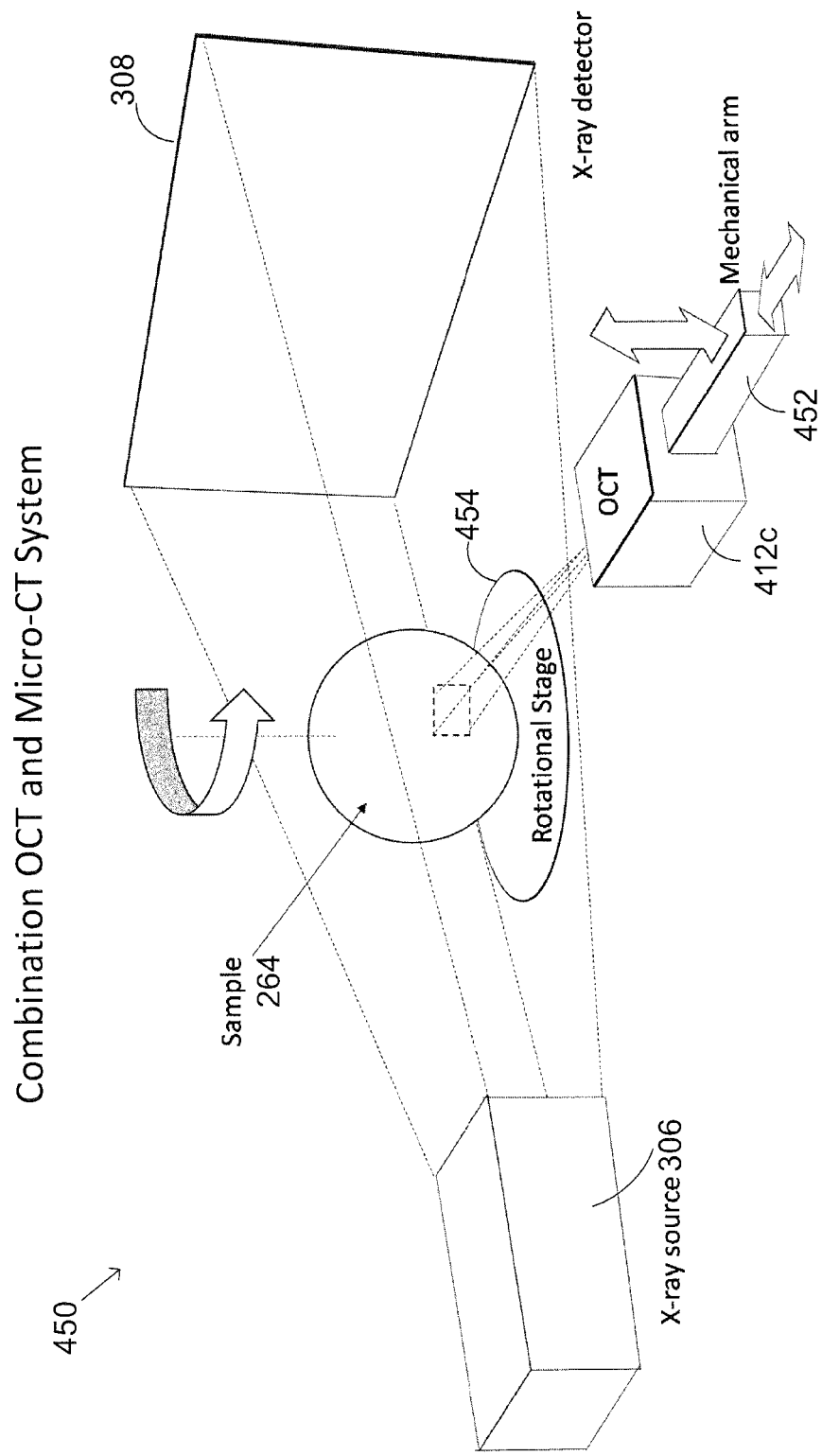
FIG. 11 is a 3D view of another example embodiment for an arrangement of imaging components for an integrated multimodal imaging system (e.g. a combination of OCT and micro-CT).

Referring now to FIG. 11, shown therein is a 3D view of another example embodiment for an arrangement of imaging components for an integrated multimodal imaging system 450. The X-ray source 306 and the X-ray detector 308 are stationary. The optical imaging portion of the system 450 is a combination of OCT and micro-CT. The OCT probe 412c is attached to one end of a mechanical arm 452. The mechanical arm 452 can be controlled to move the OCT probe 412c translationally, up or down relative to the sample 264, or forward to or away from the sample 264. The OCT probe 412c can scan the surface of the sample 264 while it rotates in the CT scanner. The system 450 further comprises a rotational sample stage 454 that can rotate the sample 264 so that different regions of the sample 264 may be imaged using the X-ray source 306 and/or the OCT probe 412c by rotating the sample stage 454.

In an example scenario, initially the OCT probe 412c can be placed outside of the field of view of the X-ray apparatus, and the rotational sample stage 454 can be rotated to a position to allow at least one X-ray image to be taken of a certain region of the sample 264. Then, the rotational sample stage 454 can be rotated, and the position of the OCT probe 312 adjusted, so that that specific region of the sample 264 can be aligned within the field of view of the OCT probe 412c. OCT image data may then be obtained for that specific region of the sample 264. When the OCT probe 412c is no longer in use, it can be moved to its initial position or to a different position outside of the field of view of the X-ray apparatus.

Figure 12:
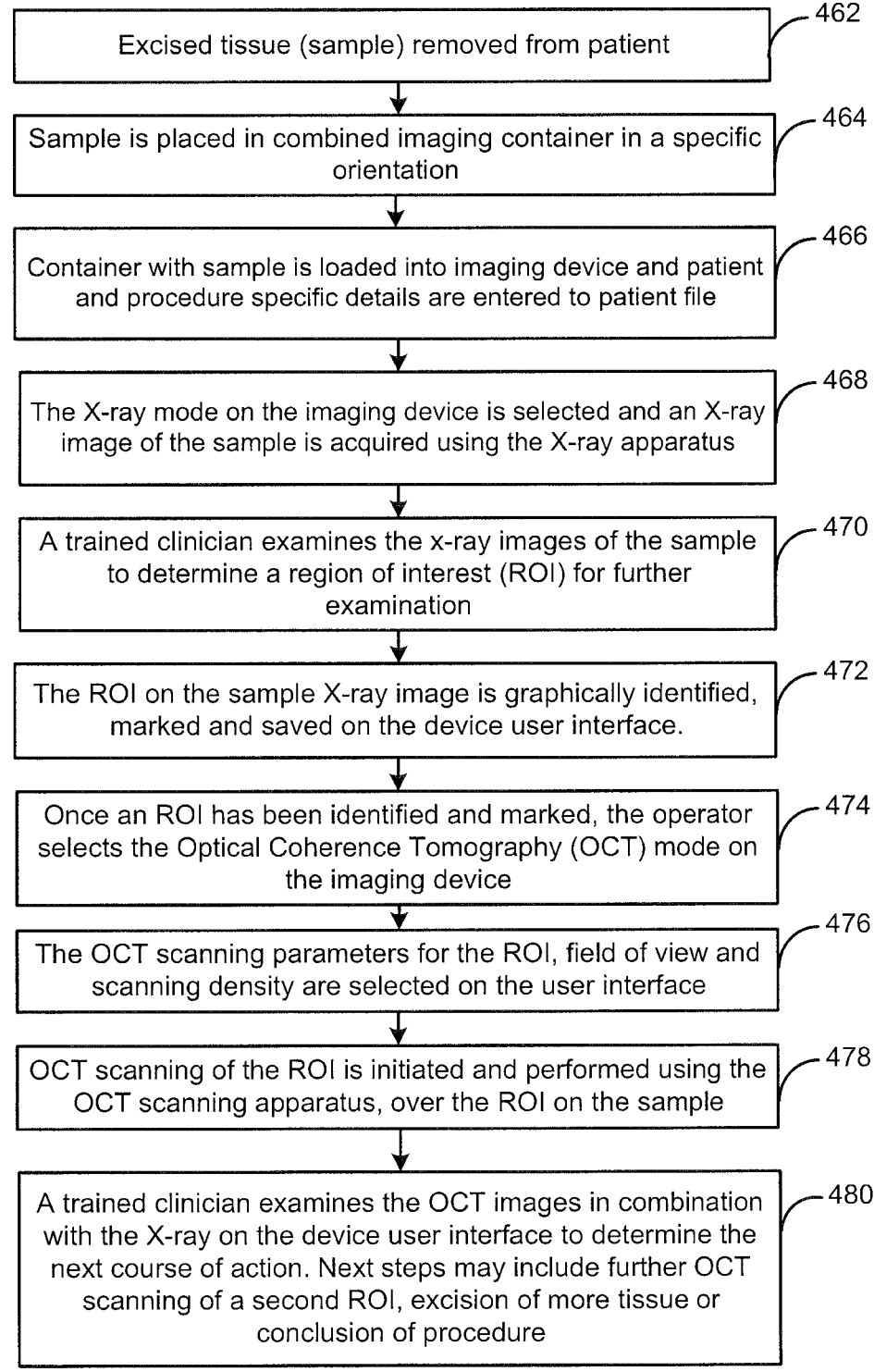
FIG. 12 shows a flowchart of an example embodiment of a method for spatial registration of multimodal images obtained in an integrated multimodal imaging system.

Referring now to FIG. 12, shown therein is a flowchart of an example embodiment of a method 470 for spatial registration of multimodal images obtained in an integrated multimodal imaging system. It should be noted that the flowchart illustrates only one example embodiment for the method 470 and there can be other embodiments in which different actions may be included or some actions may be removed depending on the particular application of the method 460.

At 462, a sample 264 of excised tissue is resected. At 464, the sample 264 is placed into a sample container (see, for example, the shared sample container 262 in FIG. 7) in a specific orientation. At 466, the container with the sample 264 is loaded into the imaging chamber of one of the integrated X-ray and OCT imaging systems 300a, 300b, 400a or 400b described herein. At 468, a user of the system (e.g., a medical practitioner such as a surgeon) can select the X-ray mode on the system via its software interface and acquire at least one X-ray image of the sample using the X-ray apparatus.

Figure 14A:
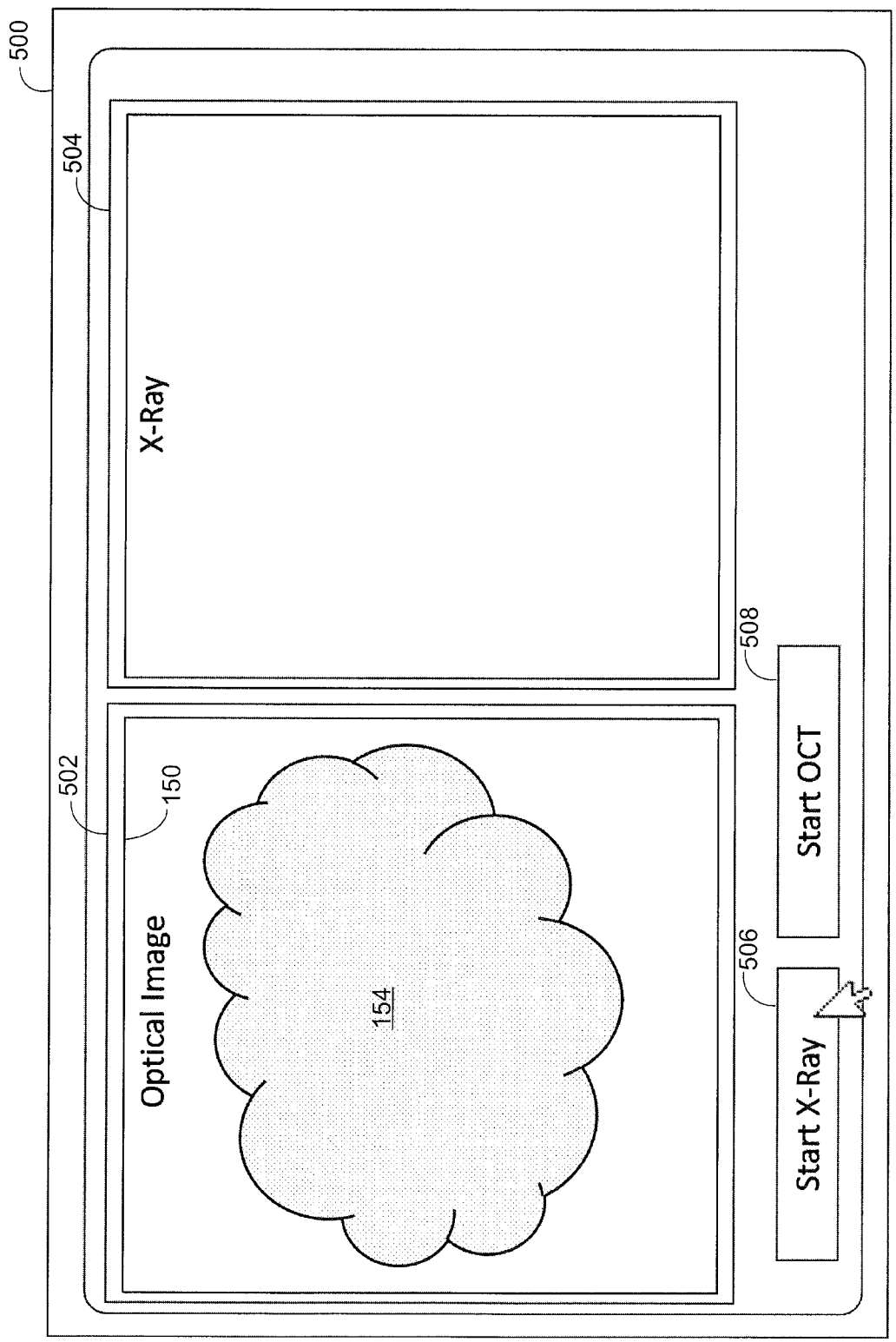
FIG. 14A shows an example embodiment of a software interface of an integrated multimodal imaging system showing an optical image of a sample.
Figure 14B:
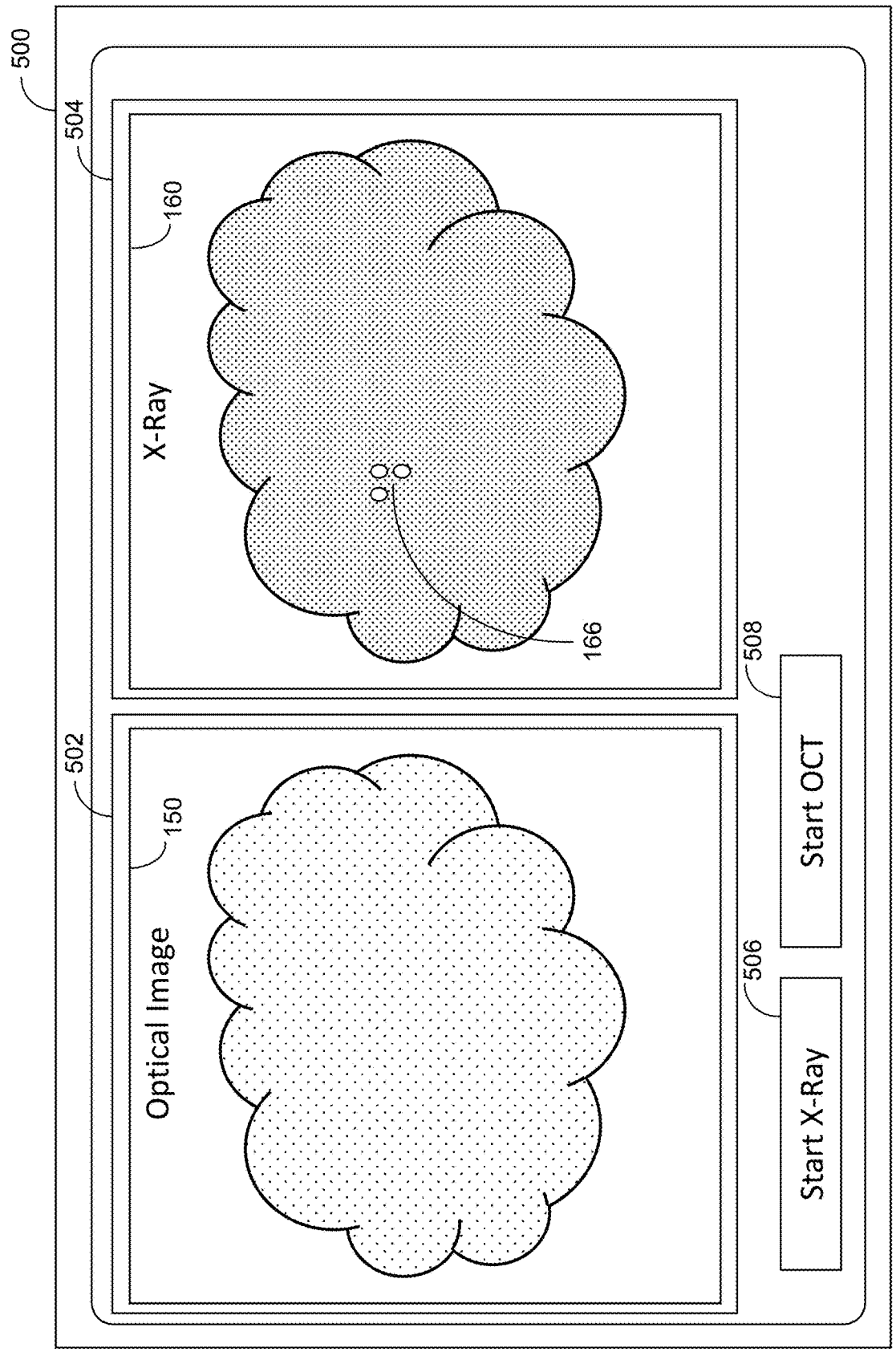
FIG. 14B shows an example of the software interface of FIG. 14A showing an X-ray image that is co-registered with the optical image.
Figure 14C:
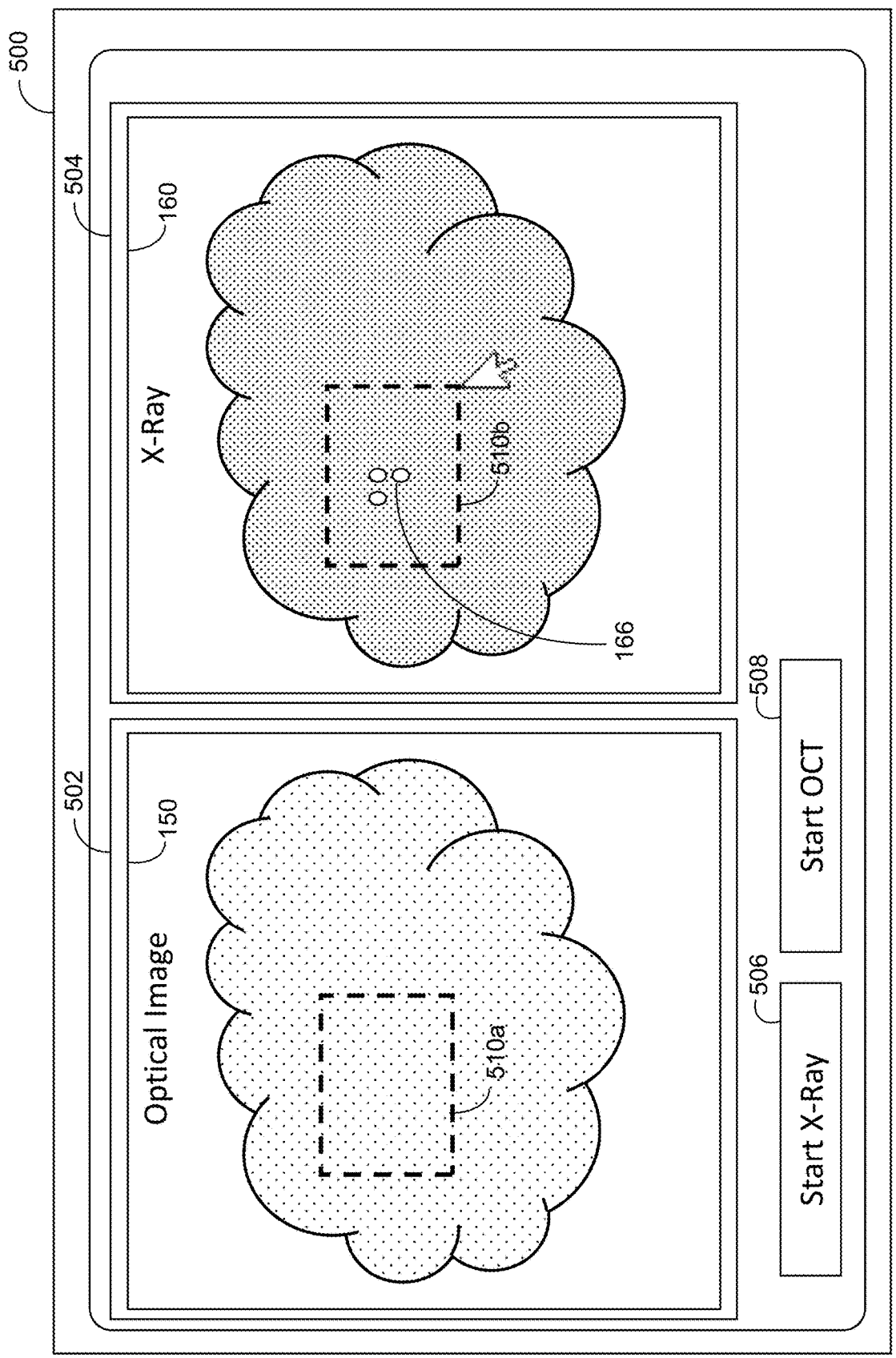
FIG. 14C shows an example of the software interface of FIG. 14B showing a highlighted ROI of the sample in at least one of the optical image and the X-ray image.

FIGS. 14A-14E show example schematic views of the software interface of the system. In general, as shown in FIGS. 14A-14C, the software interface has a main window 500, a sub-window 502 for displaying images obtained from one modality (e.g. optical images), and a sub-window 504 for displaying images obtained from another modality (e.g. X-ray images). The software interface in FIGS. 14A-14C also includes a button 506 to start obtaining image data for one imaging modality (e.g. X-ray imaging) and a button 508 to start obtaining image data for another imaging modality (e.g. OCT imaging). Initially, sub-window 502 can show a live video of the sample 264. Then, when either button 506 or 508 is pressed to initiate an X-ray or OCT scan, the next frame of the live video can be saved as the corresponding optical image of the sample 264.

Corresponding to act 468 in FIG. 12, FIG. 14A shows the sub-window 502 displaying a previously obtained optical image 150 of the sample 264, the sub-window 504 being empty, and the user proceeding to click the "Start X-Ray" button 506 to obtain an X-ray image of the sample.

Referring again now to FIG. 12, at 470 a user (e.g., a trained clinician) can examine the one or more X-ray images of at least a portion of the sample 264 that have been obtained to determine an ROI for further examination. The ROI can be determined based on features identified in the one or more X-ray images. For example, calcification in the sample 264 is generally easy to identify using x-ray. Regions of calcification can be identified in a 2D X-ray image, and those regions can later be microscopically imaged using the OCT system to see if unhealthy tissue is extending to the surface of the sample 264. FIG. 14B, which is an example schematic of the software interface showing co-registered optical and X-ray images 150 and 160, shows calcifications 166 in the X-ray image 160 of the sample 264 in the sub-window 504. Other features such as one or more of regions of high density, regions close to a surgical guide wire or surgical clips, and general abnormalities visible in an X-ray image may also be used to define an ROI depending on the type of tissue that is being imaged and the type of information about the tissue that is being sought.

Referring again to FIG. 12, at 472 the user can graphically identify an ROI by marking it using the software interface, and saving it in a data store of the multimodality imaging system. In some embodiments, a touch screen can be used, so the user can trace out an ROI having an arbitrary shape on the screen using their fingers. Alternatively, a predefined shape (such as a triangle, square, ellipse, circle or lasso shape) may be pre-specified and the user may be able to select the predefined shape, position it on the X-ray image 160 and change its size to select the ROI. In some embodiments, the white light image can be used to identify orientation of the ROI, by identifying ink or sutures that are on the sample 264 but are not visible in an X-ray image.

Referring now to FIG. 14C, shown therein is an example schematic of the software interface showing a highlighted ROI 510*b* on the sample X-ray image 160. The X-ray image 160 can be used to identify regions of abnormal density, or calcifications, to direct optical scanning. Alternatively, the ROI may be highlighted on the optical image (see 510*a*), based on features identifiable on the optical image. For example, a surgeon can palpate the sample, feel a mass, take note of where it is visually, and place visible landmarks in the optical image that can then be used to direct scanning.

More than one ROI may be selected on the optical image 150 and/or the X-ray image 160. Furthermore, a user can combine one or more ROIs defined using the optical image 150 and one or more ROIs using the X-ray image 160 to create one or more combined ROIs. For example, the areas from two or more ROIs can be combined to create a larger ROI by overlaying the two or more ROIs and tracing out the border of the overlaid ROIs or by drawing a box or other geometric figure that encompasses the two or more ROIs. Alternatively, exclusive subsets of the ROIs can be combined to create a set of larger ROIs depending on the features of interest and their distribution in the images.

Once an ROI has been identified and marked in software, at 474, the user can then select the OCT imaging mode for the integrated imaging system via the software interface, for example, by clicking the Start OCT button 508 shown in FIG. 14C.

At 476, the user can enter OCT scanning parameters via the software interface for scanning the ROI of the sample 464. For example, the user may select the field of view and the scanning density for OCT image data capture. Some features in the X-ray images can help the user decide which values to use for the OCT scanning parameters. For example, if there are clear regions of interest identified, the user may want to use a higher scanning density in those regions to ensure that no small focal region of disease is missed. On the other hand, if no clear region of interest is identified, the user may prefer to have a low density sampling over the whole sample to serve as a "screening" OCT scan. The user may then use the result of this OCT "screening" scan to identify a region of interest that may then be scanned again with a higher scanning density for OCT imaging. The low density scan may be more useful in cases with focally spread disease. Alternatively, in some cases, a clinician can perform a visual inspection to identify the ROI, since not diseased tissues have calcifications or higher density, so a user that is more specialized or experienced may be required to perform a visual analysis.

At 478, the user performs OCT scanning of the ROI using the OCT imaging apparatus to obtain OCT image data for one or more OCT images.

At 480, the user examines the one or more OCT images that have been obtained in combination with the one or more X-ray images displayed in the software interface to determine the next course of action. For example, further steps may include, but are not limited to, OCT scanning of a second ROI, excision of more tissue to obtain additional samples for further X-ray and OCT imaging, or providing a summary or test report of the results shown in the X-ray and OCT images.

Figure 13:
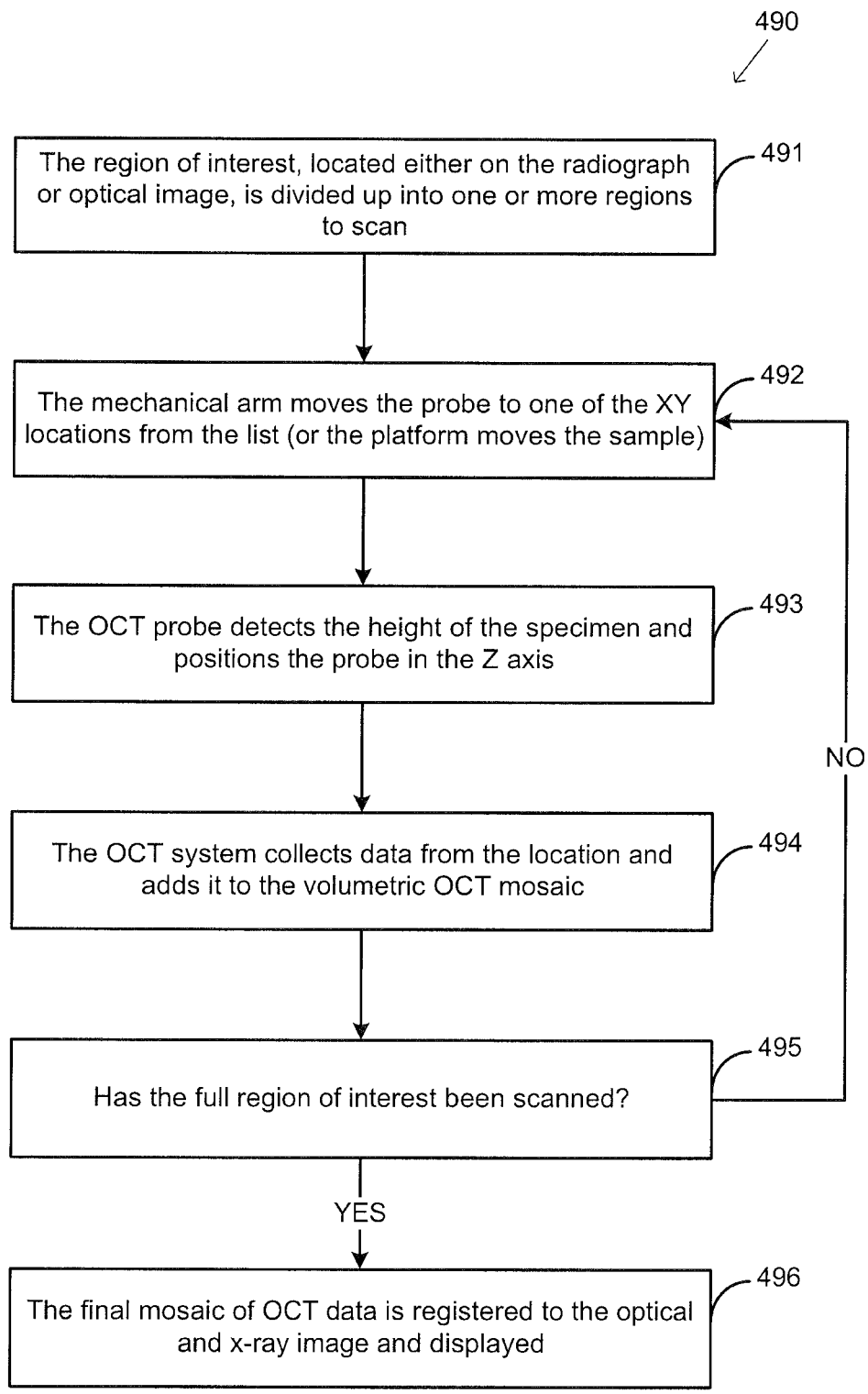
FIG. 13 shows a flowchart of an example embodiment of a method for performing OCT scanning over a selected region of interest (ROI) of an object that may be used with the method of FIG. 12.

In some embodiments, the OCT scanning of an ROI in act 478 in FIG. 12 may be conducted following a particular OCT scanning procedure such as scanning method 490 shown in FIG. 13, where the ROI is further divided into one or more sub-regions for OCT imaging.

Referring now to FIG. 13, shown therein is a flowchart of an example embodiment of scanning method 190 for performing OCT scanning over a selected ROI of an object. At 491 of method 490, the ROI is divided into sub-regions. The OCT system can define each sub-region to be an area to scan (in terms of Cartesian x, y position boundaries). For each sub-region, the OCT system can determine an initial position within the sub-region's Cartesian position boundaries, and can locate the OCT probe and the sample 464 so that OCT imaging can begin at that initial position (see act 492). This may be implemented differently depending on the OCT imaging system being used, e.g. whether the sample stage is moveable, whether the OCT probe is moveable or whether the OCT probe and the sample stage are moveable. The maximum number of sub-regions the system can support is dependent on the hardware used in the OCT probe, being a function of the mechanical mirrors and the optics used. For example, the maximum sub-window that can be subdivided has a size of 15 mm×15 mm.

At 493, the OCT system detects the height of the surface of the sample 464, determines a target position (i.e. a z position for a desired height) for the OCT probe relative to the sample surface, and then moves one of the OCT probe and the sample stage to achieve the target height position.

At 494, the OCT system obtains OCT image data of the current sub-region of the sample being imaged using the OCT probe and the target height position. The obtained OCT image data can be saved in a data store and later added to OCT image data obtained for the other sub-regions of the ROI. Acts 492-494 may be repeated until all sub-regions of the ROI have been scanned by the OCT probe.

At 495, if all sub-regions of the ROI have been scanned, the OCT image data can be combined to create an OCT image of the ROI of the sample. The combined OCT image data may be combined using a wide-field OCT imaging technique depending on the size of the ROI and the OCT imaging resolution. An example of an OCT wide-field imaging technique that may be used is described in U.S. published patent application No. 2016/0040976, which is hereby incorporated by reference in its entirety. The OCT image can then be registered to the X-ray image by aligning the Cartesian x, y positions of the OCT image and the X-ray image, and also be displayed in the software interface. The OCT image data also has additional z-axis information that shows height information. Accordingly, the OCT system provides 3D information, and the 2D cross sections are aligned to corresponding XY on the X-ray and optical images.

Figure 14D:
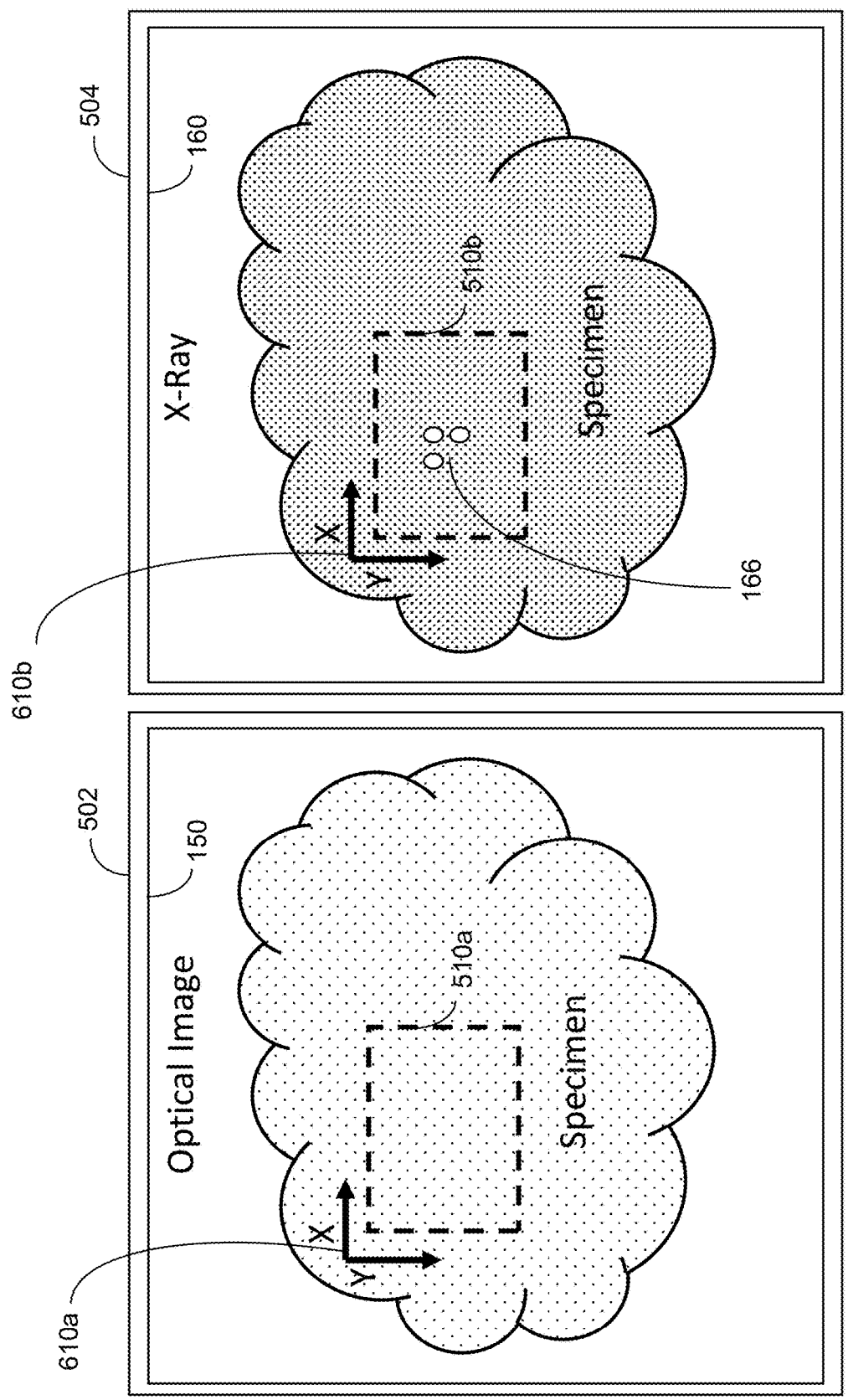
FIG. 14D shows an example of the software interface of FIG. 14C showing an X-axis and a Y-axis for a highlighted ROI of the sample in the X-ray image and the optical image.

Referring now to FIG. 14D, shown therein is an example embodiment with X and Y axes for a highlighted ROI on the optical image 150 and the co-registered x-ray image 160 for a sample. The sub-window 502 of the software interface displays the optical image 150 of the sample, the selected region of interest 510*a*, and the X and Y axes 610*a*. The sub-window 504 displays the X-ray image 160, the corresponding selected region of interest 510*b*, and the corresponding X and Y axes 610*b*.

Figure 14E:
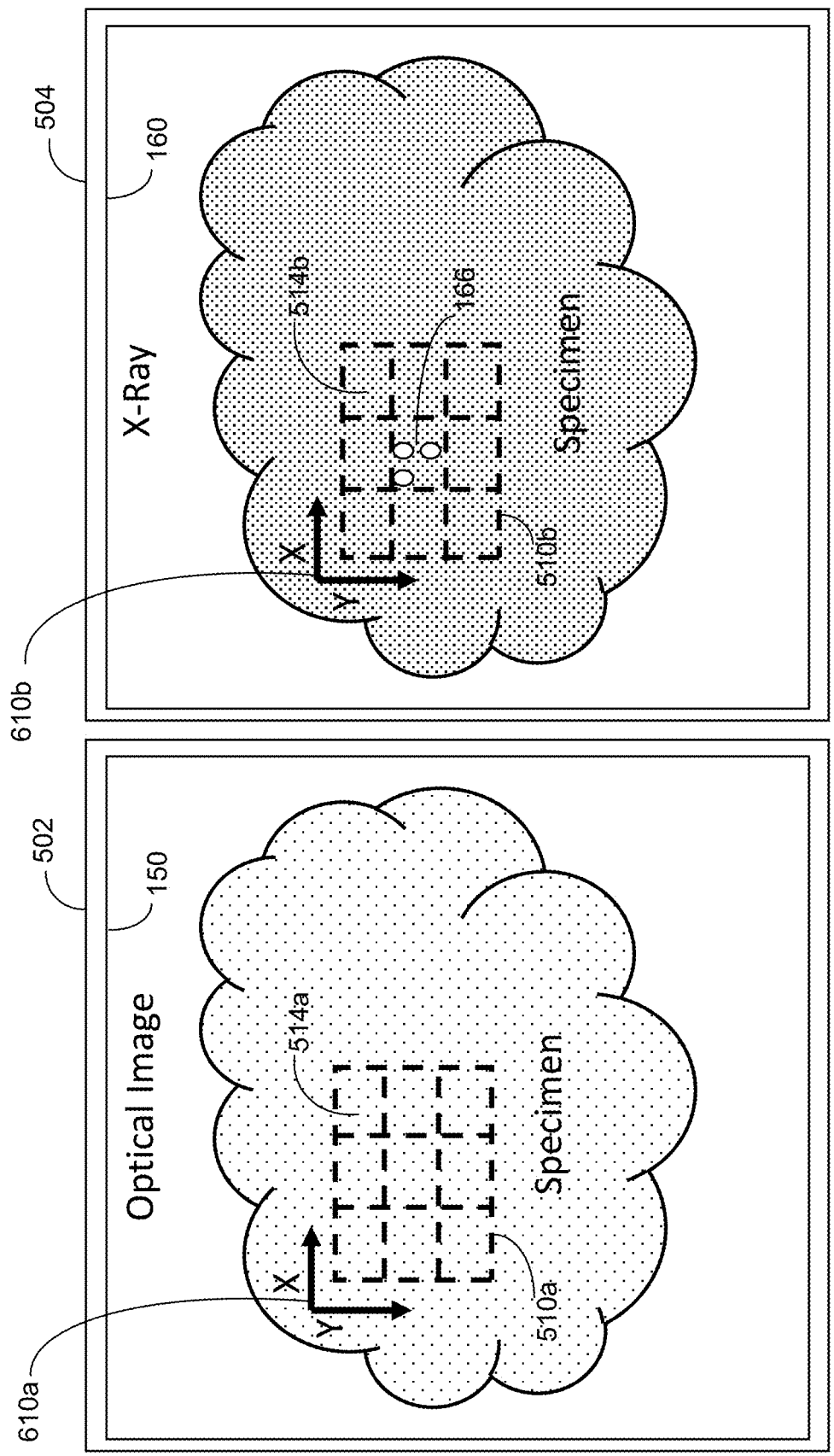
FIG. 14E shows an example of the software interface of FIG. 14D showing a further division of the ROI of the sample in the X-ray image or the optical image for obtaining OCT data.

Referring now to FIG. 14E, shown therein is an example embodiment showing a division of the ROI 514*a* on the optical image 150 and the ROI 514*b* on the co-registered X-ray image 160 for obtaining OCT data. In the case where the ROI on the optical image 150 and the ROI on the X-ray image 160 are different, these ROIs can be combined and then the sub-grids can be determined from the combined ROI. The combination of two or more ROIs results in the generation of a new ROI that contains the two or more ROIs. This new larger ROI can then be treated as individual ROIs are treated and broken up using the same sub-dividing method into sub-grids.

Figure 14F:
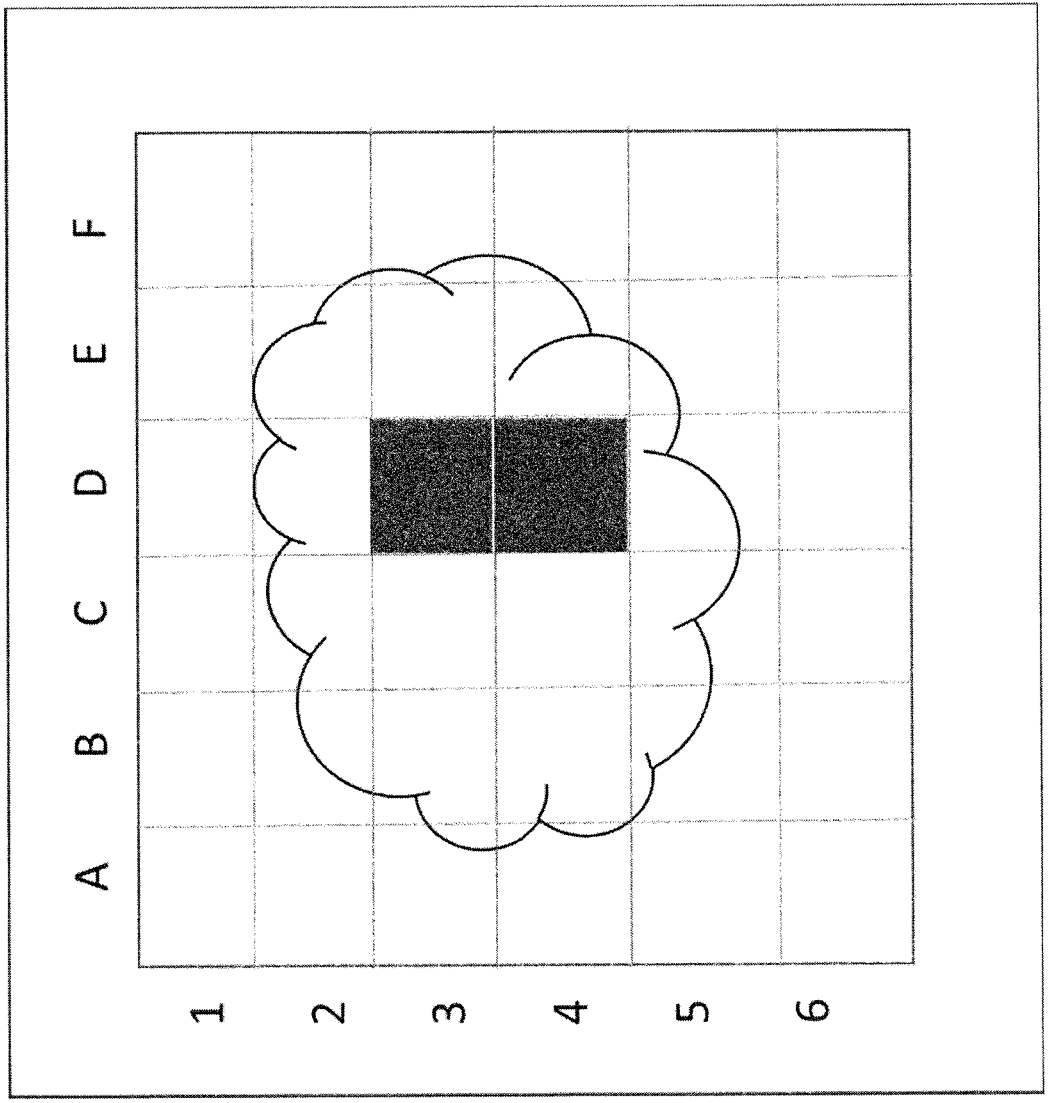
FIG. 14F shows an example of using a physical grid to assist with obtaining OCT image data for a ROI.

In some embodiments, as shown in FIG. 14F, a physical grid display may be implemented in the system's software interface to allow the user to select and mark the region of interest on either the optical image 150 or the X-ray image 160 by picking from the pre-defined boxes in the physical grid.

Figure 15A:
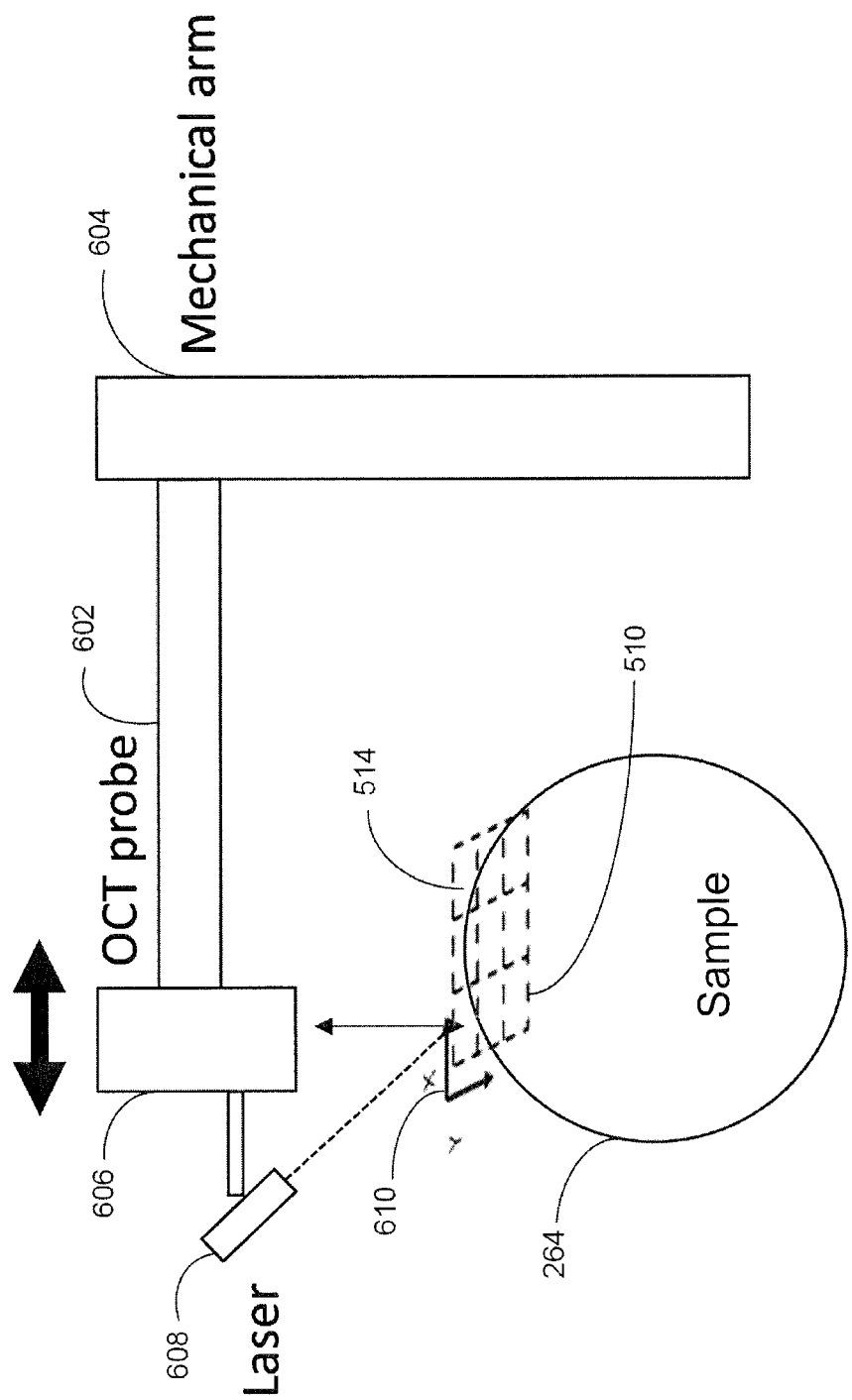
FIG. 15A shows an example alternative embodiment of a mechanism that incorporates a laser to obtain OCT image data for a target Z-axis probe position for an OCT system.

In some embodiments, as shown in FIG. 15A, the target z position for placing the OCT probe to scan at least a portion of the sample can be determined using a position measuring device. In some embodiments, the position measuring device may include an integrated optical camera built into the OCT probe 606 and one or more lasers 608 mounted to the OCT probe 606. When the OCT probe 606 is the correct distance from the target position the lasers are angled such that laser spot is in the center of the optical image generated by the integrated optical camera When the OCT probe 606 approaches the sample 264, the optical camera may be used to take optical images of the sample 264. For height positioning, the laser beam from 608 is visible on the surface of the sample 164 and the optical camera is used to detect the laser spot. The system is calibrated such that when the OCT probe 606 is at a correct distance from a target, the laser spot is in the center of the image. This is done by setting the angle of the laser 608 so that it is directed to the sample 264 and then adjusting the OCT probe 606 until it is at the proper height. During scanning, the probe height is adjusted to a new location until the light spot (e.g. laser spot) is in the center of the camera image, ensuring that the OCT probe 606 is at the desired offset distance. Once the OCT probe 606 is at the desired offset distance, OCT data is recorded for that position. For example, a laser having a certain color may be used and to find where the laser spot is in the optical image, the image can be filtered according to the color, the filtered image can be compared to a threshold (for example, 80% of the maximum value) and the centroid of the pixels above the threshold can be determined to find where the center of the laser spot is.

Figure 15B:
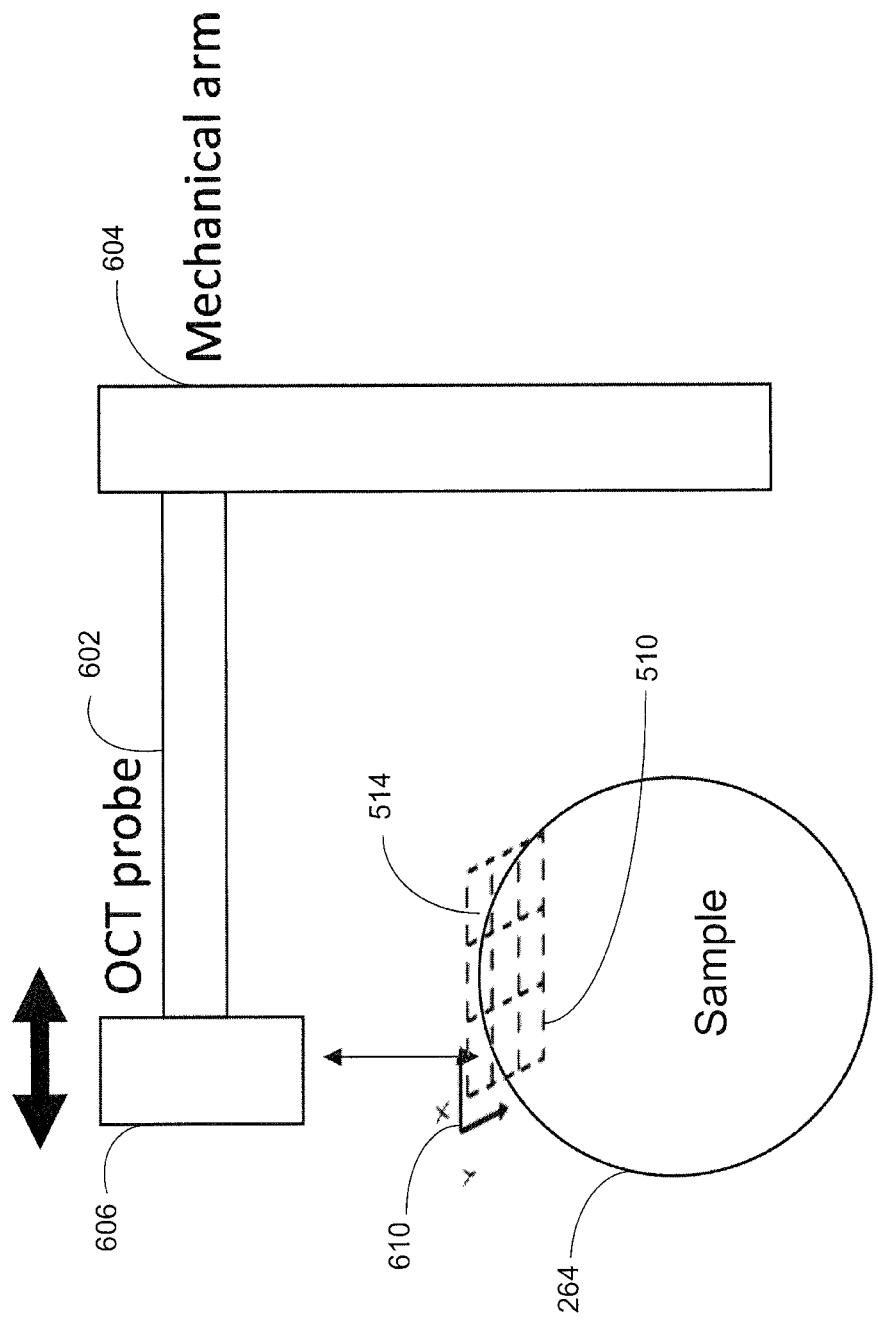
FIG. 15B shows an example alternative embodiment of a mechanism used to obtain OCT image data for a target Z-axis probe position for an OCT system.

In some other embodiments, as shown in FIG. 15B, no additional hardware is required for the OCT system to detect the surface of the sample 264 and determine the target z position for the OCT probe 606. For example, the OCT probe 606 can continue approaching the sample 264 while acquiring OCT data. At each acquisition, the maximum signal detected in the acquired OCT data can be compared to a predefined threshold. This may be continued repeatedly until the detected maximum signal has crossed the predefined threshold, at which point the system can conclude that the OCT probe 606 is at the desired z position and stop probe movement and OCT data acquisition. The OCT data can then be recorded for that position. In some embodiments, the predefined threshold can be set to 80% of the maximum signal intensity. Ideally a signal point measurement can be used for this calibration, and then the full OCT image can be acquired afterwards. However, in some embodiments full images may be used for this calibration process.

Figure 16A:
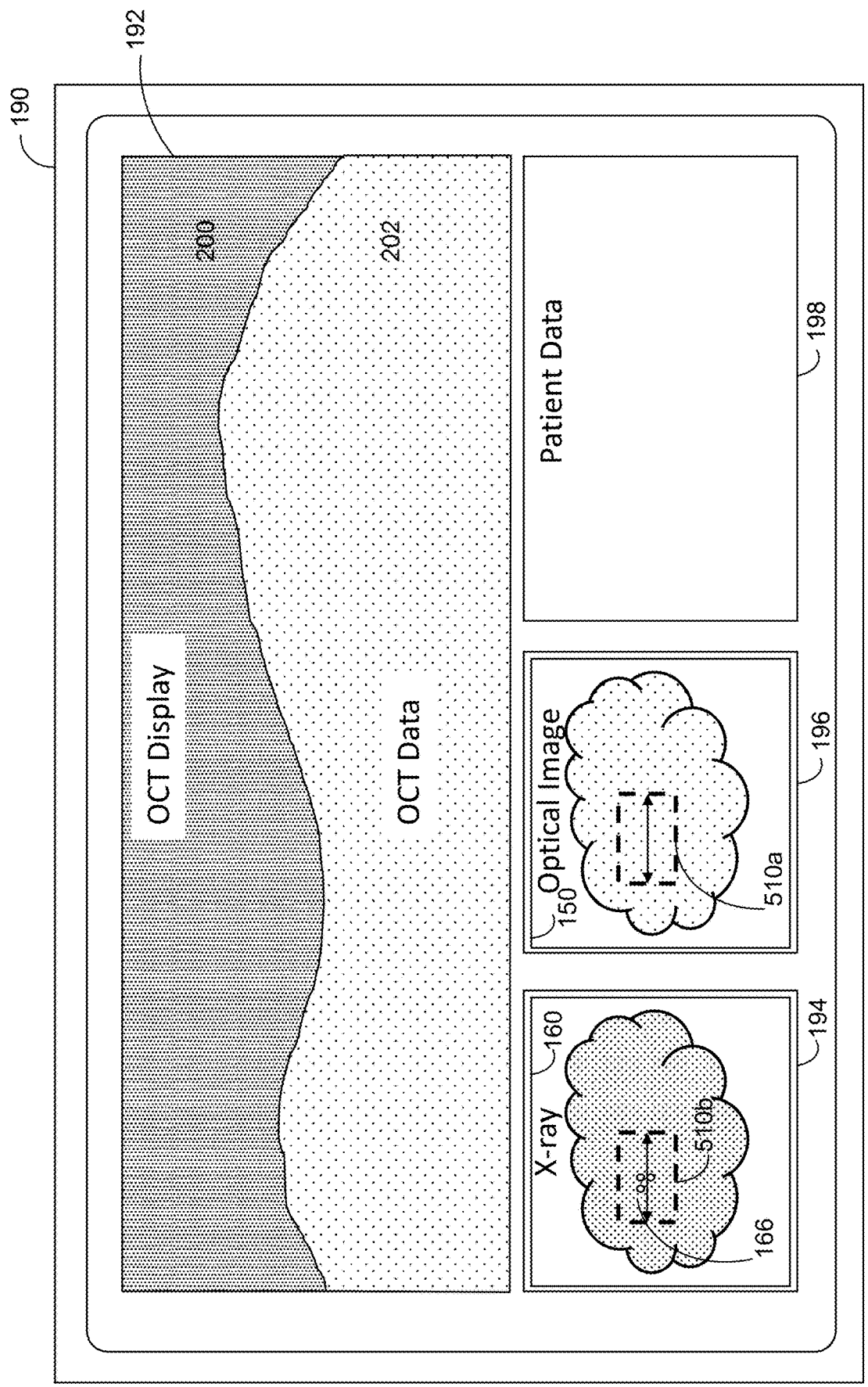
FIG. 16A shows an example schematic of a software interface for an integrated multimodal imaging system showing spatially registered X-ray and optical images without using fiducial markers, and corresponding OCT data for an ROI (the horizontal arrows in the X-ray view and the optical view show where the OCT data is taken for the ROI).

Referring now to FIG. 16A, shown therein is an example embodiment of the software interface of an integrated multimodal imaging system for displaying multimodal imaging results. The results show spatially registered X-ray and optical images 160 and 150, without using fiducial markers, and corresponding OCT data for an ROI (the horizontal arrows in the X-ray view and optical view show where the OCT data is taken for the ROI). In this example embodiment, fiducial markers are not needed because the OCT and X-ray devices share the same physical reference frame/orientation.

Figure 16B:
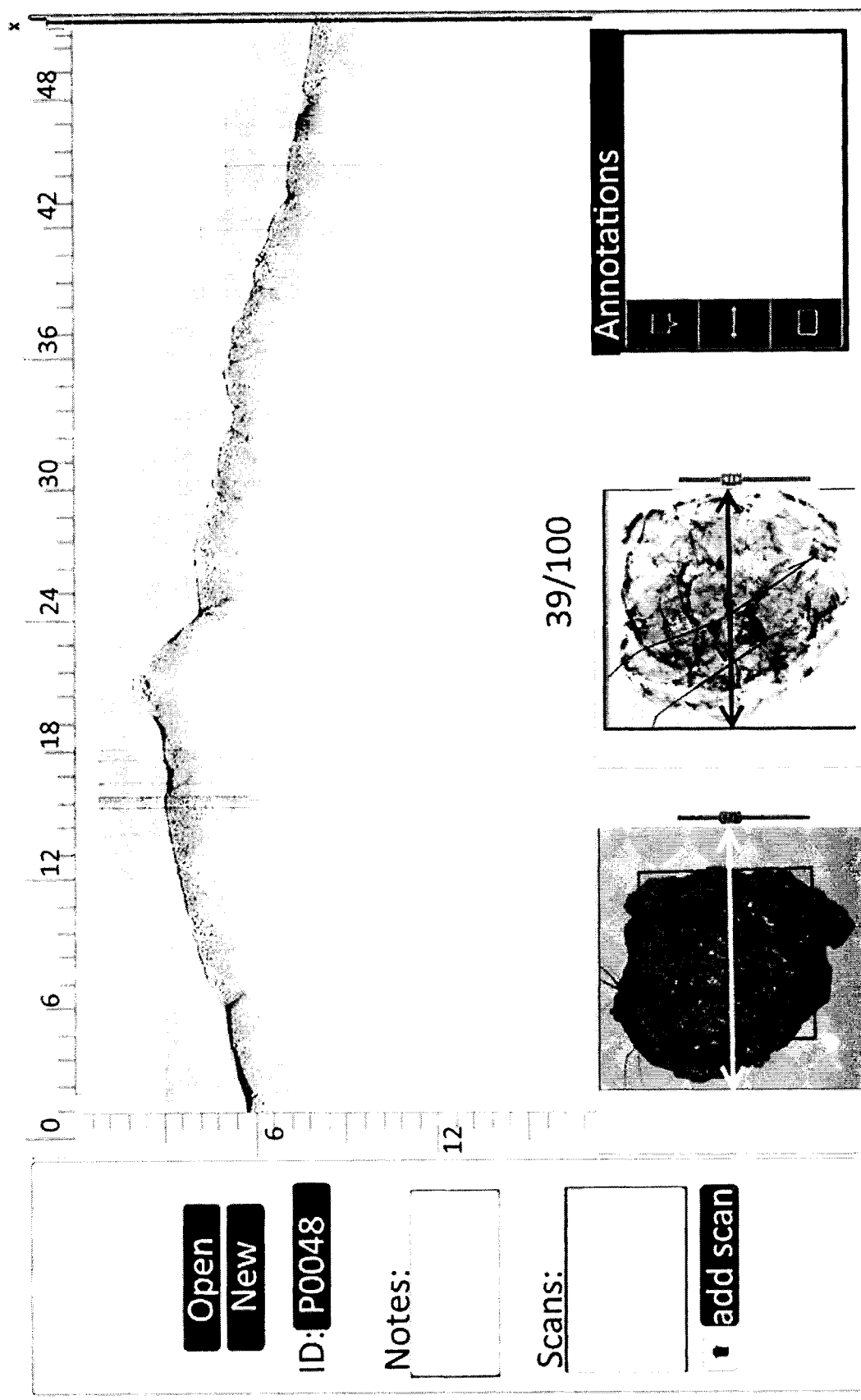
FIG. 16B shows an example embodiment of a software interface for an integrated X-ray and OCT imaging system.

The results are shown using a main window 190 having a first sub-window 194 wherein an X-ray image 160 of at least a portion of the sample 264 is displayed, a second sub-window 196 where the co-registered optical image 150 of at least a portion of the sample is displayed, a third sub-window 198 where additional patient information such as patient medical record number (MRN) and patient name may be displayed, and an OCT display sub-window 192 for displaying the obtained OCT data showing the surface of the sample (see the boundary line between 200 and 202) for at least a portion of the ROI. The horizontal arrows in the X-ray image 160 and the optical image 150 show where the OCT data is taken, which in this example is where calcifications 166 are visible in the X-ray image 160. FIG. 16B shows an example of the interface main window 190 with actual data.

It should be noted that various embodiments of systems, processes and devices have been described herein by way of example only. It is not intended that the applicant's teachings be limited to such embodiments. On the contrary, the applicant's teachings described and illustrated herein may encompass various alternatives, modifications, and equivalents, without departing from the spirit and scope of the embodiments described herein, which is limited only by the appended claims, which should be given the broadest interpretation consistent with the description as a whole.

The invention claimed is:

1. An integrated system for generating at least one X-ray image and at least one optical image of at least a portion of a sample, wherein the integrated system comprises:
    an imaging area having a sample stage for receiving a sample;
    an X-ray apparatus disposed within the imaging area, the X-ray apparatus being configured to acquire X-ray image data of the at least a portion of the sample;
    a microscopic imaging apparatus disposed within the imaging area, the microscopic imaging apparatus being configured to acquire optical image data of the at least a portion of the sample and microscopic image data of the at least a portion of the sample;
    a processor configured to be in electrical communication with the X-ray apparatus and the microscopic imaging apparatus, the processor being operable to:
    control the X-ray apparatus to acquire the X-ray image data of the at least a portion of the sample, and generate an X-ray image from the X-ray image data of the at least a portion of the sample;
    control the microscopic imaging apparatus to acquire the optical image data of the at least a portion of the sample, and generate an optical image from the optical image data of the at least a portion of the sample:
    co-register the X-ray image and the optical image;
    determine a region of interest (ROI) of the at least a portion of the sample based on at least one of the X-ray image and the optical image; and
    control the microscopic imaging apparatus to acquire microscopic image data of the ROI, and generate an Optical Coherence Tomography (OCT) image of the ROI from the microscopic image data of the ROI.

2. The integrated system of claim 1, wherein the X-ray apparatus comprises an X-ray generator and an X-ray detector, wherein the X-ray generator and the X-ray detector are positioned on opposite sides of the sample stage.

3. The integrated system of claim 1, wherein the microscopic imaging apparatus is configured to perform one of OCT imaging, Optical Coherence Microscopy imaging, Confocal Microscopy imaging, Spectrally-Encoded Confocal Microscopy (SECM) imaging, or fluorescence SECM imaging.

4. The integrated system of claim 1, wherein the microscopic imaging apparatus comprises an OCT imaging apparatus that comprises an OCT probe oriented towards the sample stage for scanning the at least a portion of the sample during use.

5. The integrated system of claim 4, wherein the OCT probe is disposed above the sample stage or below the sample stage.

6. The integrated system of claim 4, wherein the OCT probe is pivotally adjustable with respect to the sample stage.

7. The integrated system of claim 4, further comprising a first translation mechanism for shifting the OCT probe in a first linear direction with respect to the sample stage.

8. The integrated system of claim 7, further comprising a second translation mechanism for shifting the OCT probe in a second linear direction with respect to the sample stage, the second linear direction being substantially perpendicular to and co-planar with the first linear direction.

9. The integrated system of claim 4, wherein the processor is further configured to:
    divide the ROI into one or more sub-regions of the sample;
    control the OCT imaging apparatus according to OCT imaging parameters to acquire OCT image data of each sub-region of the one or more sub-regions of the sample,
    wherein the microscopic image data comprises the OCT image data of each sub-region of the one or more sub-regions of the sample; and
    generate an OCT image based on the OCT image data from the one or more sub-regions of the sample.

10. The integrated system of claim 9, wherein the processor is further configured to create an OCT mosaic image using the OCT image data of each sub-region of the one or more sub-regions of the sample, and wherein the OCT image comprises the OCT mosaic image.

11. The integrated system of claim 9, wherein the processor is further configured to adjust a scanning density to obtain the OCT image data of each sub-region of the one or more sub-regions of the sample within a specified time limit for performing OCT scanning.

12. The integrated system of claim 1, wherein the sample stage comprises a rotational sample stage capable of manipulating a position of the sample by applying a rotational movement.

13. The integrated system of claim 12, wherein the rotational sample stage is configured to manipulate the position of the sample to a first position aligned within a field of view of the X-ray apparatus and to manipulate the position of the sample to a second different position aligned within a field of view of the microscopic imaging apparatus.

14. The integrated system of claim 1, further comprising an enclosure for housing the imaging area, the X-ray apparatus, the microscopic imaging apparatus, and the processor.

15. The integrated system of claim 1, further comprising a user interface configured to be in electrical communication with the processor, wherein the user interface is physically isolated from the imaging area to prevent a contamination of the sample during use, and the user interface is configured to receive input values that correspond to the ROI and optionally X-ray imaging parameters, and optionally microscopic imaging parameters.

16. The integrated system of claim 1, further comprising a compression plate that is moveable towards the sample stage to compress the sample during imaging.

17. An integrated system for generating at least one X-ray image and at least one Optical Coherence Tomography (OCT) image of at least a portion of a sample, wherein the integrated system comprises:
    an imaging area having a sample stage for receiving a sample;
    an X-ray apparatus disposed within the imaging area, the X-ray apparatus being configured to acquire X-ray image data of the at least a portion of the sample;
    an OCT imaging apparatus disposed within the imaging area, the OCT imaging apparatus being configured to acquire OCT image data of the at least a portion of the sample, the OCT imaging apparatus comprising an OCT probe oriented towards the sample stage for scanning the at east a portion of the sample during use; and
    a processor configured to be in electrical communication with the X-ray apparatus and the OCT imaging apparatus, the processor being operable to:
    control the X-ray apparatus to acquire the X-ray image data of the at least a portion of the sample, and generate one or more X-ray images from the X-ray image data of the at least a portion of the sample;

determine a region of interest (ROI) of the at least a portion of the sample based on the one or more X-ray images;

divide the ROI into one or more sub-regions of the sample;

control the OCT imaging apparatus according to OCT imaging parameters to acquire sub-region OCT image data of each sub-region of the one or more sub-regions of the sample; and generate an OCT image based on the sub-region OCT image data of each sub-region of the one or more sub-regions of the sample.

18. A method for generating at least one X-ray image and at least one optical image of at least a portion of a sample, wherein the method comprises:

positioning a sample on a sample stage within an imaging, area;

acquiring X-ray image data of at least a portion of the sample and generating an X-ray image from the X-ray image data of the at least a portion of the sample;

acquiring an optical image data of the at least a portion of the sample and generating an optical image from the optical image data of the at least a portion of the sample;

co-registering the X-ray image and the optical image;

determining a region of interest (ROI) of the at least a portion of the sample based on at least one of the X-ray image and the optical image; and acquiring microscopic image data of the ROI and generating an Optical Coherence Tomography (OCT) image of the ROI from the microscopic image data of the ROI.

19. The method of claim 18, wherein the acquiring microscopic image data of the ROI comprises:

performing OCT imaging of the ROI;

specifying a time limit for performing OCT imaging of the ROI; and adjusting a scanning density to obtain OCT image data within the time limit, wherein the microscopic image data of the ROI comprises the OCT image data; and the generating an OCT image of the ROI from the microscopic image data of the ROI comprises:

dividing the ROI into one or more sub-regions;

acquiring OCT image data for each sub-region of the one or more sub-regions; and generating the OCT image of the ROI using the OCT image data of each sub-region of the one or more sub-regions.

20. The method of claim 19, wherein the acquiring the OCT image data for each sub-region of the one or more sub-regions comprises:

determining an initial position for an OCT probe;

moving at least one of the OCT probe and the sample stage to place the OCT probe at the initial position;

determining a target position for the OCT probe;

moving the OCT probe to focus on the target position; and acquiring the OCT image data of each sub-region of the one or more sub-regions.

21. The method of claim 20, wherein the determining the target position for the OCT probe comprises:

directing a laser beam from one or more lasers to center of a scanning window of the OCT probe when the OCT probe is at the initial position;

moving the OCT probe towards the sample and taking optical images of the sample using an optical imaging device;

adjusting the target position for the OCT probe once a laser spot is in view of the optical imaging device; and recording the target position for the OCT probe once the laser spot appears at a target point on the sample.

* * * * *